US008778649B2

(12) United States Patent
Parales et al.

(10) Patent No.: US 8,778,649 B2
(45) Date of Patent: Jul. 15, 2014

(54) USE OF ACIDOTHERMUS CELLULOLYTICUS XYLANASE FOR HYDROLYZING LIGNOCELLULOSE

(71) Applicant: The Regents of the University of California, Oakland, CA (US)

(72) Inventors: Rebecca E. Parales, Davis, CA (US); Alison M. Berry, Davis, CA (US); Juanito V. Parales, Jr., Davis, CA (US); Ravi D. Barabote, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/653,328

(22) Filed: Oct. 16, 2012

(65) Prior Publication Data
US 2013/0295619 A1 Nov. 7, 2013

Related U.S. Application Data

(62) Division of application No. 12/613,398, filed on Nov. 5, 2009, now abandoned.

(60) Provisional application No. 61/203,528, filed on Dec. 22, 2008.

(51) Int. Cl.
| | | |
|---|---|---|
| *C12Q 1/34* | (2006.01) | |
| *C12P 19/14* | (2006.01) | |
| *C12N 9/24* | (2006.01) | |
| *C07K 14/00* | (2006.01) | |
| *C12P 21/00* | (2006.01) | |

(52) U.S. Cl.
CPC ............. *C12P 19/14* (2013.01); *C12N 9/2482* (2013.01); *C12Y 302/01008* (2013.01)
USPC ............. 435/200; 435/18; 435/69.1; 530/350

(58) Field of Classification Search
USPC .................... 435/200, 69.1, 72, 18
See application file for complete search history.

(56) References Cited

U.S. PATENT DOCUMENTS

| | | | |
|---|---|---|---|
| 4,966,850 A | 10/1990 | Yu et al. | |
| 5,395,765 A | 3/1995 | Dahlberg et al. | |
| 5,437,992 A | 8/1995 | Bodie et al. | |
| 5,736,384 A | 4/1998 | Fukunaga et al. | |
| 5,902,581 A | 5/1999 | Clarkson et al. | |
| 5,935,836 A | 8/1999 | Vehmaanpera et al. | |
| 6,083,733 A | 7/2000 | Gronberg et al. | |
| 7,060,482 B1 | 6/2006 | Sung et al. | |
| 7,226,772 B2 | 6/2007 | Hseu et al. | |
| 2005/0000666 A1 | 1/2005 | Taylor et al. | |

OTHER PUBLICATIONS

Wong et al., Microbiological Reviews 52(3):305-317, 1988.*
Shiang et al., Applied Microbiology and Biotechnology 34:591-597, 1991.*
Mohagheghi et al., International Journal of Systematic Bacteriology 36(3):435-443, 1986.*
Office Action received for Chinese Patent Application No. 200980151311.5, mailed on Sep. 26, 2012, 12 pages (7 pages of English Translation and 5 pages of Chinese Office Action).
Extended European Search Report received for European Patent Application No. 09835430.1, mailed on Jun. 4, 2012, 4 pages.
Office Action received for New Zealand Patent Application No. 593541, mailed on Jul. 22, 2011, 2 pages.
Office Action received for New Zealand Patent Application No. 593541, mailed on Nov. 6, 2012, 1 page.
International Preliminary Report on Patentability received for PCT Patent Application No. PCT/US2009/063444, mailed on Jul. 7, 2011, 6 pages.
Barabote et al., "Complete Genome of the Cellulolytic Thermophile Acidothermus Cellulolyticus 11B Provides Insights into its Ecophysiological and Evolutionary Adaptations", Gene Bank accession No. ABK52146.1, 2009, 2 pages.
Office Action received for Chinese Patent Application No. 200980151311.5, mailed on Mar. 26, 2013, 10 pages (6 pages of English Translation and 4 pages of Office Action).
Non Final Office Action received for U.S. Appl. No. 12/613,398, mailed on May 24, 2012, 22 pages.
International Search Report and Written Opinion received for PCT Patent Application No. PCT/US2009/63444, mailed on Mar. 16, 2010, 8 pages.
Branden et al., "Introduction to Protein Structure," Garland Publishing Inc., New York, 1991, p. 247.
Copeland et al., "Complete Sequence of Acidothermus Cellulolyticus 11B", Accession No. A0LRT6, Dec. 12, 2006 (Online), Retrieved on Mar. 5, 2010, Available at <http://www.uniprot.org/uniprot/A0LRT6.html>.
Rubin, Edward M., "Genomics of Cellulosic Biofuels", Nature, vol. 454, Aug. 14, 2008, pp. 841-845.
Seffernick et al., "Melamine Deaminase and Atrazine Chlorohydrolase: 98 Percent Identical but Functionally Different" Journal of Bacteriology, vol. 183, No. 8, Apr. 2001, pp. 2405-2410.
Witkowski et al., "Conversion of a β-Ketoacyl Synthase to a Malonyl Decarboxylase by Replacement of the Active-Site Cysteine with Glutamine" Biochemistry, vol. 38, 1999, pp. 11643-11650.
Office Action received for Indonesian Patent Application No. WO0201102656, mailed on Aug. 16, 2013, 3 pages.
Office Action received for Australian Patent Application No. 2009330641, mailed on Mar. 13, 2014, 4 pages.
Office Action received for Chinese Patent Application No. 200980151311.5, issued on Mar. 19, 2014, 12 pages (7 pages of English Translation).

* cited by examiner

*Primary Examiner* — Delia Ramirez
(74) *Attorney, Agent, or Firm* — Morrison & Foerster LLP

(57) ABSTRACT

A thermophilic endo-beta-1,4-xylanase derived from *Acidothermus cellulolyticus* is disclosed. The xylanase exhibits xylanase activity at an optimal temperature of 90° C. and an optimal pH range of about 4.5-6.0. The isolated xylanase is useful in the hydrolysis of lignocellulosic material.

11 Claims, 23 Drawing Sheets

| Organism | MW (kDa) | T opt (range) | pH opt (range) | Thermostability | Patent#; Inventor(s); Year; (Company) |
|---|---|---|---|---|---|
| Acidothermus cellulolyticus | 50-55 | 70-80 | (3.6 - 4.2) | >5 h at 90 C | 5902581; Clarkson et al., 1999 (Genencor International, Inc.) |
| Bacillus sp. (208 & 2113) | 22.5 | 70 (50-80) | 8 (5-8) |  | 5736384; Fukunaga et al 1998, (New Oji Paper Company Ltd.) |
| Bacillus sp. (208 & 2113) | 32 | 80 (60-80) | 5 (5-8) |  | 5736384; Fukunaga et al 1998, (New Oji Paper Company Ltd.) |
| Thermococcus auranticus |  | 75 (70-80) | 5 (4.8-5.8) | 12 weeks at 90 C | 4966850; Ernest, et al 1980 (Farinex Canada Corp.) |
| Microtetraspora flexuosa | 33 | 70 | 7-7.5 | 110 min at 80C | 5437992; Bodie et al 1995 (Genencor International, Inc.) |
| Microtetraspora flexuosa | 13.3 | 65 | 7-7.5 | 45 min at 80C | 5437992; Bodie et al 1995 (Genencor International) |
| Microtetraspora flexuosa | 31 | 65 | 7.5 | 30 min at 80C | 5437992; Bodie et al 1995 (Genencor International) |
| Microtetraspora flexuosa | 50 | 65 | 7.5 | 90 min at 80C | 5437992; Bodie et al 1995 (Genencor International) |
| Microtetraspora flexuosa | 35 | 70 | 7.5 | 30 min at 80C | 5437992; Bodie et al 1995 (Genencor International) |
| Rhodothermus marinus |  | 80 (85-100) | 6 (5-8) | >3 h at 80 C & pH 7 | 5459765; Dahlberg et al 1995 (Novo Nordisk A/S) |
| Several xylanases from anaerobic thermophilic bacteria |  | 60-70 | 6 (5-7) | 10 min – 2 h at 80 C & pH 9 or pH 7 | 6083733; Grossberg et al., 2000 (Gist-brocades B.V.) |
| Trichoderma reesei recombinant xylanases |  | 50 | 4-6 | >60 min at 80 C | 7060482; Sung & Tolan 1906 (National Research Council of Canada) |
| Actinomadura flexuosa | 85 | 70-80 | 6-7 | >24 h at 70 C pH 6 | 5935836; Vehmaanperä et al., 1999, (Roihm Enzyme Finland Oy) |
| Actinomadura flexuosa | 50 | 70-80 | 6-7 | >24 h at 70 C pH 6 | 5935836; Vehmaanperä et al., 1999, (Roihm Enzyme Finland Oy) |

Fig. 1 (Prior Art)

```
                                                                    cggcaa    (SEQ ID NO: 4)
                                                                    gccgtt    (SEQ ID NO: 5)

ttcgttcacgttgaggggtgacggcgtcggttgccccgcagtaggcgtccgtctgtcccgcagtaggcgtcctgaagaatttcgagaaaatttcgacaacgtggaggaatgcg
gtctgtcccgtaagaatttccgaaaatttcggacaacgtggaggaatgcgcagacaggcgattcttaaagcctgtgcacctcctacgc ATGAGAATGCGCTCGATGACGGCAGCGGCTGGCGCTGGCCATGGTCGTCGCCATGGTGGTGGCCACCGCCTTTGCGCACGGCTTTCGCCACGGCAATCCGCCTACCACCGC      (SEQ ID NO: 3)
TACTCTTACGCGAGCTACTGCCGTCGCCGCCGACGCTGCCAGGCGCTGCCAGGCGGTGCCGTGGCGGCATGGTGGGCG
 M   R   M   R   S   M   T   A   A   L   G   A   A   M   V   V   A   T   T   A   F   A   H   G   N   P   P   Y   H   P CGGGCCGATTCGCTCCGGCCTCCGGCTGCTGGAAGATAGGCTCTGACCTCGACCATCCGCCATCATTCCGCGTACCGCGGATCCGGATTACGCGGCAATCGC
GCCCGGGTAAGCGAGGCGCGACCGACCAGGCTTCTATCCGGAGGCGCATGCCAGGCATGCCAGCCATGGCGGTAGTAAGGCATGCTGGAGCTGGAGCTAATGCGCCGTTAGCG
 P   A   D   S   L   R   A   L   A   A   K   I   G   L   R   V   G   T   A   I   I   P   Y   D   L   D   H   P   D   Y   A   A   I   A CGCCAGTCAATTCTCGGTCGTCACCCCAGGCAACGAAATGAAGTGGCAGGTCGTTGAACCGACCCAGACCAGCTCGGTCCGGCGGCGATCGGCTC
GCGGTCAGTTAAGAGCCAGCCAGTGGGGTCCGTTGCTTACTTCACCGTCCAGCAACTTGGCTGGGTCCATGCTAACCAGCCGCCGCTAGCCGAG
 A   S   Q   F   S   V   V   T   P   G   N   E   M   K   W   Q   V   V   E   P   T   Q   G   T   Y   D   W   S   G   G   D   R   L GTGCAATTCGCGCAAGAACACGGACTCGTCCGGGCCCACACGGTCTGCTGGCACAACCAGCTCCCCGACTGCTGTCAGGGCTCAACAACGGTA
CACGTTAAGCGCGTTCTTGTCCTGTCGAGCGAGCAGCAGCCGTGTTGGCAGCAGCAGCAGTGTCGACCAGCAGTTGTTGCCAT
 V   Q   F   A   Q   E   H   G   Q   L   V   R   G   H   T   L   V   W   H   N   Q   L   P   D   W   L   V   Q   G   V   N   N   G CGATTTCCAACGCGGCCAATTGCCGGACCTGCTGCACAAGCACATCGTGGACCAAGTCACCGTTCAAAGGAAAGATCTCGCAATGACGTCGCAATGA
GCTAAAGGTTGCGCGTTACGCCCGGACCTGGACGACGTGTTCGTAGCACCTGCTTCAGTGGTAAGTTTCCTTTCAGACCGTTACCCTGCAGCGCTTACT
 T   I   S   N   A   Q   L   R   D   L   L   H   K   H   I   V   D   E   V   T   H   F   K   G   K   I   W   Q   W   D   V   A   N   E ATTCTTCGGCCAACTCCTGGACCCCCATCCACTCCCCGACCCGCATCAACGGAGACGATTCTGGGTGCAGCATCCTCGGTGAGGGAATCATCGCGACGCC
TAAGAAGCCGGTTGAGGACCCTGGGCGTAGGTGAGGGCTGCCTAGTTGCCTCTGCTAAAGACCCACGTCGTAGAGCCACTCCCTAGTTAGGGCGTCGGG
 F   F   A   N   S   W   D   P   H   P   L   P   D   G   I   N   G   D   D   F   W   V   Q   H   L   G   E   G   I   I   A   D   A TTCCGGGCGCCACCAGCGCCCATCGGCACGCCCCGTCGTCTTCTACAACGACTACAACATCGCCGGCGAAGACGGCACGAACGCCAAGGCCGACGCCGTGT
AAGGCGACCCGCGGTGGTCGGCTGCCTAGGCGTGCCGACAACAAGATGTTGCTGATGTTGTAGACGTGTAGCGCCGACAACAACAACGACGACG
 F   R   W   A   H   Q   A   D   P   H   A   L   F   Y   N   D   Y   N   I   A   G   E   D   G   T   N   A   K   A   D   A   V
```

Fig. 6 (A), 6 (B), and 6 (C)

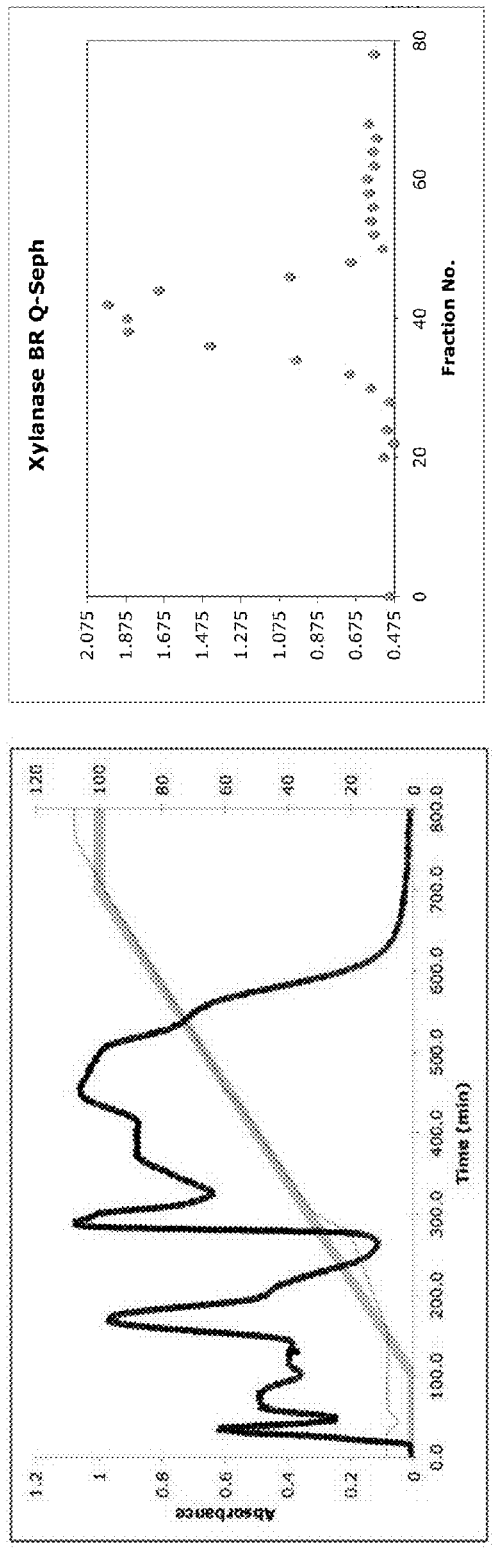
Fig. 8 (A) and 8 (B)

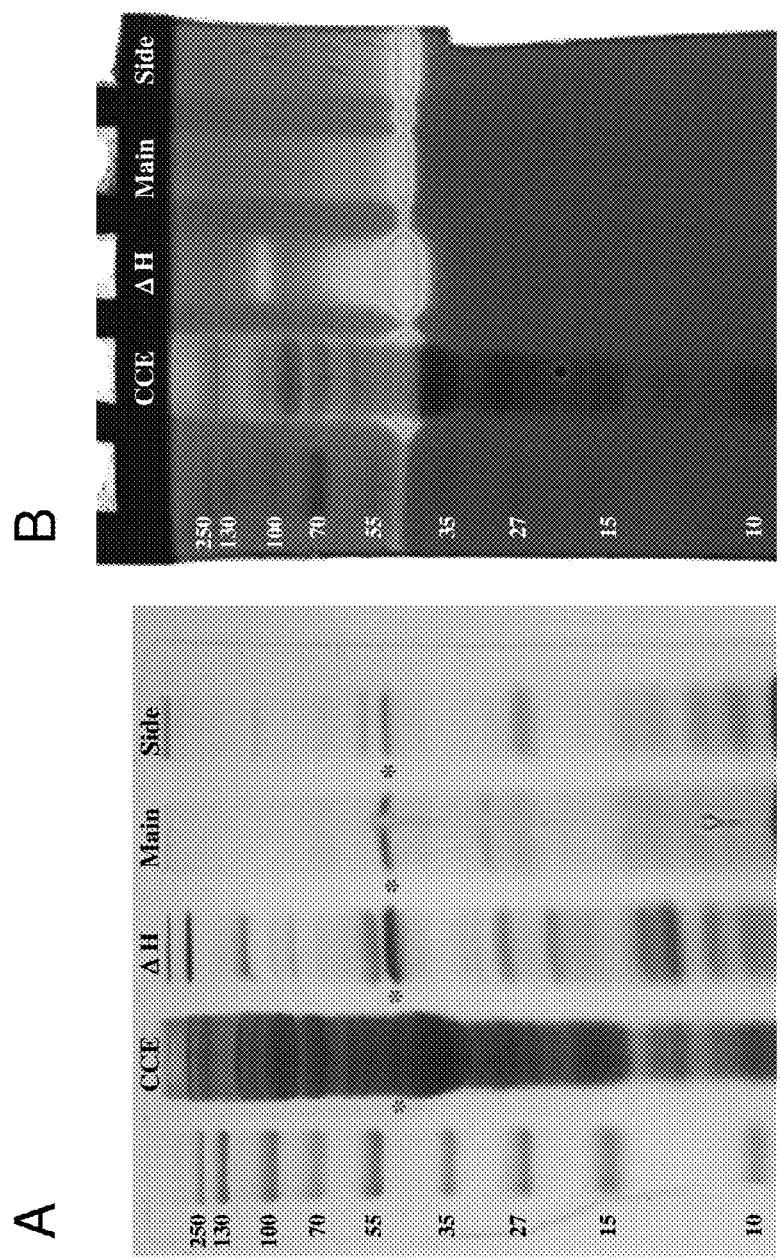
Fig. 9 (A) and 9 (B)

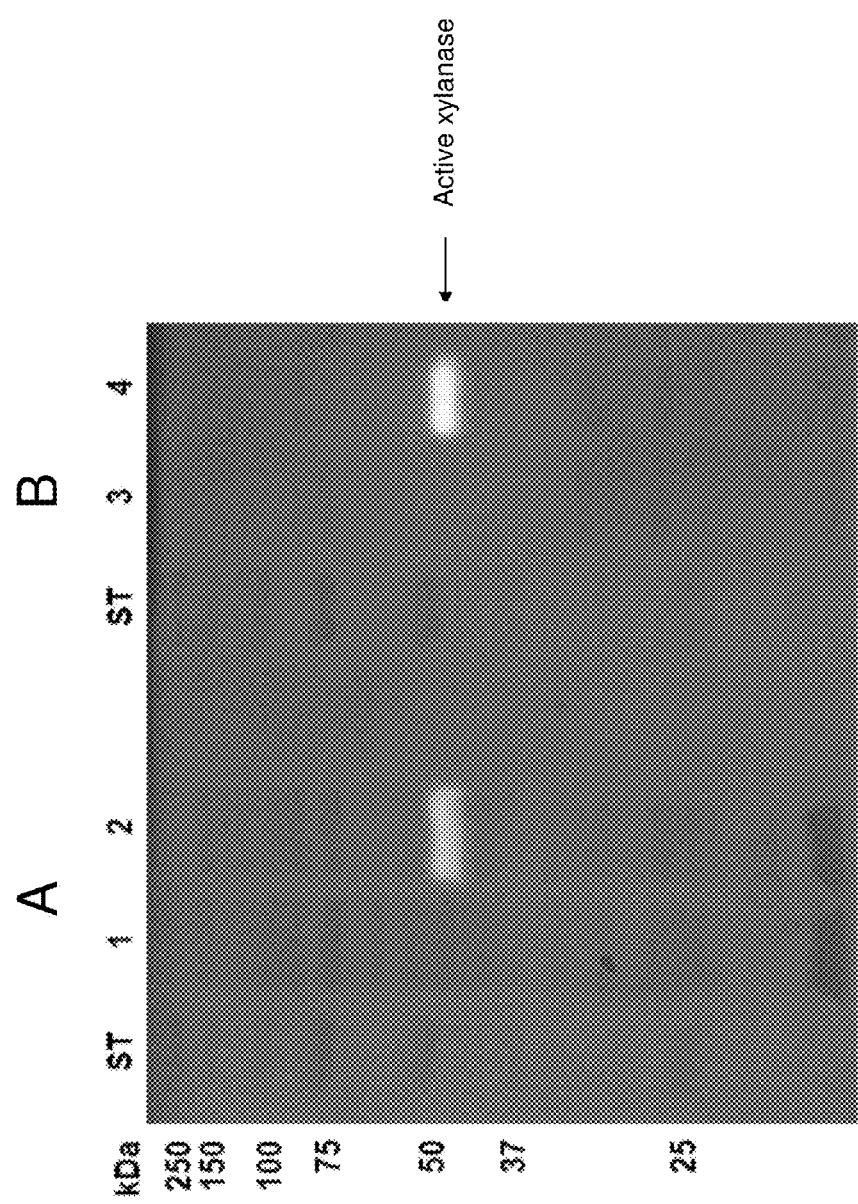
Fig. 13 (A) and 13 (B)

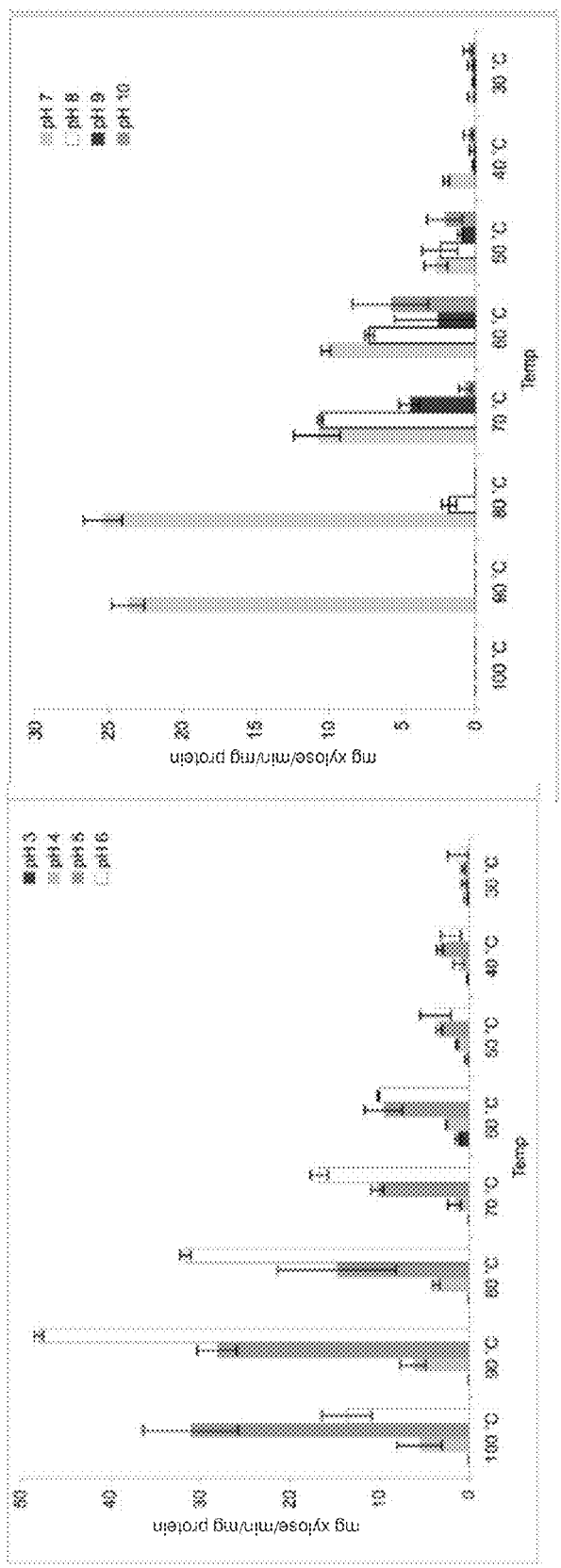
Fig. 20 (A) and 20 (B)

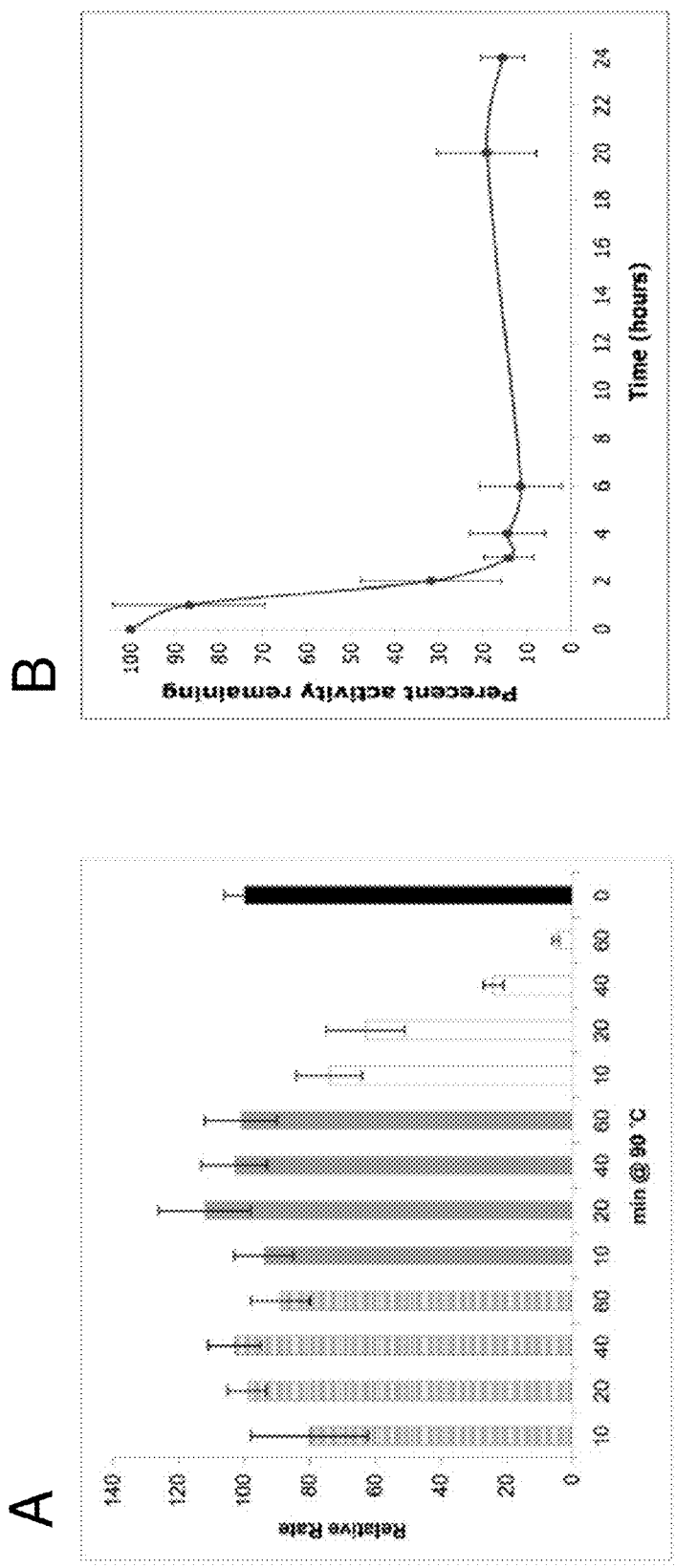
Fig. 21 (A) and 21 (B)

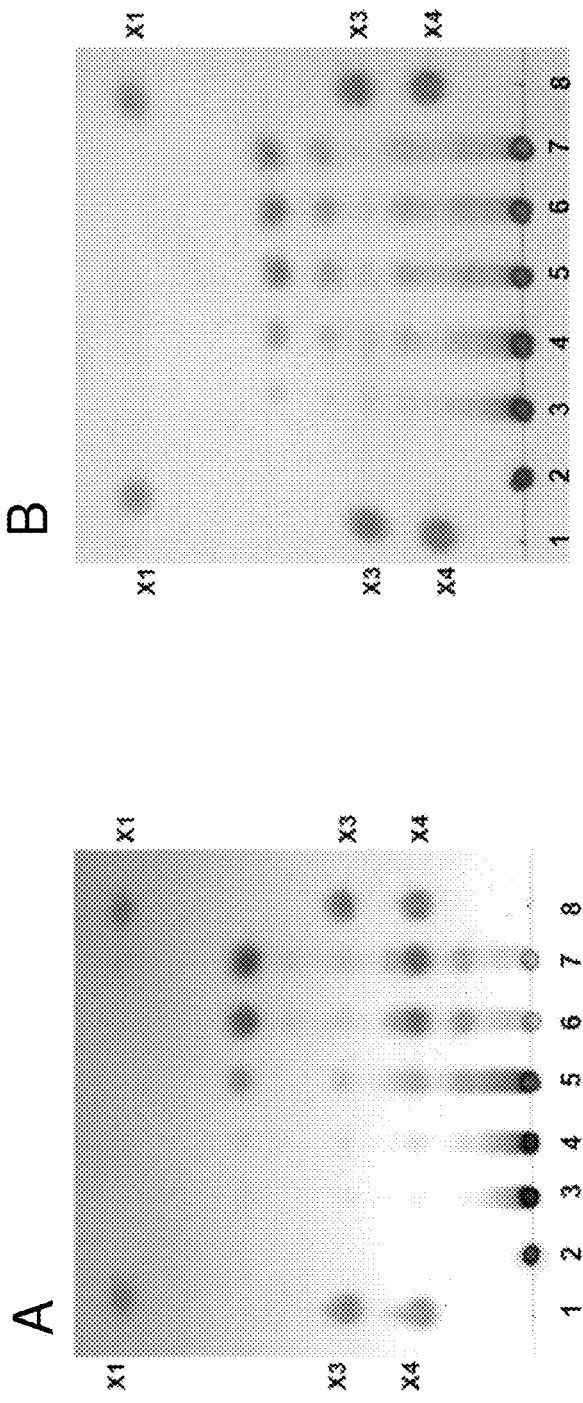
Fig. 22 (A) and 22 (B)

SEQUENCE LISTING

<160> NUMBER OF SEQ ID NOS: 40

<210> SEQ ID NO 1
<211> LENGTH: 364
<212> TYPE: PRT
<213> ORGANISM: Acidothermus cellulolyticus

<400> SEQUENCE: 1

```
His Gly Asn Pro Pro Tyr His Pro Pro Ala Asp Ser Leu Arg Ala Leu
 1               5                  10                  15

Ala Ala Lys Ile Gly Leu Arg Val Gly Thr Ala Ile Ile Pro Tyr Asp
             20                  25                  30

Leu Asp His Pro Asp Tyr Ala Ala Ile Ala Ala Ser Gln Phe Ser Val
         35                  40                  45

Val Thr Pro Gly Asn Glu Met Lys Trp Gln Val Val Glu Pro Thr Gln
     50                  55                  60

Gly Thr Tyr Asp Trp Ser Gly Gly Asp Arg Leu Val Gln Phe Ala Gln
 65                  70                  75                  80

Glu His Gly Gln Leu Val Arg Gly His Thr Leu Val Trp His Asn Gln
                 85                  90                  95

Leu Pro Asp Trp Leu Val Gln Gly Val Asn Asn Gly Thr Ile Ser Asn
            100                 105                 110

Ala Gln Leu Arg Asp Leu Leu His Lys His Ile Val Asp Glu Val Thr
        115                 120                 125

His Phe Lys Gly Lys Ile Trp Gln Trp Asp Val Ala Asn Glu Phe Phe
    130                 135                 140

Ala Asn Ser Trp Asp Pro His Pro Leu Pro Asp Gly Ile Asn Gly Asp
145                 150                 155                 160

Asp Phe Trp Val Gln His Leu Gly Glu Gly Ile Ile Ala Asp Ala Phe
                165                 170                 175

Arg Trp Ala His Gln Ala Asp Pro His Ala Leu Leu Phe Tyr Asn Asp
            180                 185                 190

Tyr Asn Ile Ala Gly Glu Asp Gly Thr Asn Ala Lys Ala Asp Ala Val
        195                 200                 205

Tyr Asn Trp Val Lys Lys Met Leu Ala Glu Gly Val Pro Ile Asn Gly
    210                 215                 220

Ile Gly Asp Gln Gly His Leu Asp Thr Gln Tyr Gly Phe Pro Thr Lys
225                 230                 235                 240

Met Gln Glu Asp Leu Gln Arg Tyr Ala Asp Leu Gly Leu Lys Val Ala
                245                 250                 255

Ile Thr Glu Ala Asp Val Arg Thr Phe Val Thr Asp Ala Thr Thr Gln
            260                 265                 270

Gln Pro Thr Asp Pro Leu Ala Pro Tyr Ala Gln Ala Asn Tyr Tyr Asp
        275                 280                 285

Gly Met Leu Lys Ala Cys Leu Ala Val Lys Asn Cys Ile Ser Tyr Thr
```

```
            290                 295                 300
Val Trp Gly Phe Gly Asp Ala Asp Ser Trp Ile Pro Gly Phe Phe Ser
305                 310                 315                 320

Gly Glu Gly Tyr Ala Asn Leu Tyr Asp Val Asn Leu Gln Pro Lys Pro
                325                 330                 335

Ala Tyr Thr Ala Leu Gln Gln Thr Leu Ala Leu Ala Ala Gly Ala Pro
                340                 345                 350

His Arg Ala Gly Phe Gly His His Ala Leu Arg Arg
            355                 360

<210> SEQ ID NO 2
<211> LENGTH: 25
<212> TYPE: PRT
<213> ORGANISM: Acidothermus cellulolyticus

<400> SEQUENCE: 2

Met Arg Met Arg Ser Met Thr Ala Ala Ala Leu Gly Ala Ala Met Val
1               5                   10                  15

Val Ala Thr Ala Thr Thr Ala Phe Ala
            20                  25

<210> SEQ ID NO 3
<211> LENGTH: 389
<212> TYPE: PRT
<213> ORGANISM: Acidothermus cellulolyticus

<400> SEQUENCE: 3

Met Arg Met Arg Ser Met Thr Ala Ala Ala Leu Gly Ala Ala Met Val
1               5                   10                  15

Val Ala Thr Ala Thr Thr Ala Phe Ala His Gly Asn Pro Pro Tyr His
            20                  25                  30

Pro Pro Ala Asp Ser Leu Arg Ala Leu Ala Ala Lys Ile Gly Leu Arg
        35                  40                  45

Val Gly Thr Ala Ile Ile Pro Tyr Asp Leu Asp His Pro Asp Tyr Ala
    50                  55                  60

Ala Ile Ala Ala Ser Gln Phe Ser Val Val Thr Pro Gly Asn Glu Met
65                  70                  75                  80

Lys Trp Gln Val Val Glu Pro Thr Gln Gly Thr Tyr Asp Trp Ser Gly
                85                  90                  95

Gly Asp Arg Leu Val Gln Phe Ala Gln Glu His Gly Gln Leu Val Arg
            100                 105                 110

Gly His Thr Leu Val Trp His Asn Gln Leu Pro Asp Trp Leu Val Gln
        115                 120                 125

Gly Val Asn Asn Gly Thr Ile Ser Asn Ala Gln Leu Arg Asp Leu Leu
    130                 135                 140

His Lys His Ile Val Asp Glu Val Thr His Phe Lys Gly Lys Ile Trp
145                 150                 155                 160

Gln Trp Asp Val Ala Asn Glu Phe Phe Ala Asn Ser Trp Asp Pro His
                165                 170                 175

Pro Leu Pro Asp Gly Ile Asn Gly Asp Asp Phe Trp Val Gln His Leu
            180                 185                 190

Gly Glu Gly Ile Ile Ala Asp Ala Phe Arg Trp Ala His Gln Ala Asp
        195                 200                 205

Pro His Ala Leu Leu Phe Tyr Asn Asp Tyr Asn Ile Ala Gly Glu Asp
    210                 215                 220

Gly Thr Asn Ala Lys Ala Asp Ala Val Tyr Asn Trp Val Lys Lys Met
```

```
                225                 230                 235                 240
Leu Ala Glu Gly Val Pro Ile Asn Gly Ile Gly Asp Gln Gly His Leu
                245                 250                 255

Asp Thr Gln Tyr Gly Phe Pro Thr Lys Met Gln Glu Asp Leu Gln Arg
                260                 265                 270

Tyr Ala Asp Leu Gly Leu Lys Val Ala Ile Thr Glu Ala Asp Val Arg
                275                 280                 285

Thr Phe Val Thr Asp Ala Thr Thr Gln Gln Pro Thr Asp Pro Leu Ala
                290                 295                 300

Pro Tyr Ala Gln Ala Asn Tyr Tyr Asp Gly Met Leu Lys Ala Cys Leu
305                 310                 315                 320

Ala Val Lys Asn Cys Ile Ser Tyr Thr Val Trp Gly Phe Gly Asp Ala
                325                 330                 335

Asp Ser Trp Ile Pro Gly Phe Phe Ser Gly Glu Gly Tyr Ala Asn Leu
                340                 345                 350

Tyr Asp Val Asn Leu Gln Pro Lys Pro Ala Tyr Thr Ala Leu Gln Gln
                355                 360                 365

Thr Leu Ala Leu Ala Ala Gly Ala Pro His Arg Ala Gly Phe Gly His
                370                 375                 380

His Ala Leu Arg Arg
385

<210> SEQ ID NO 4
<211> LENGTH: 1441
<212> TYPE: DNA
<213> ORGANISM: Acidothermus cellulolyticus

<400> SEQUENCE: 4
cggcaattcg ttcacgttga ggggttgacg gcgtcggttg ccccgcagta gcgtccgtct      60
gtcccgtaag aatttccgaa aatttcggac acggtggagg aatgcgatga gaatgcgctc     120
gatgacggca gcggcgctgg gcgctgccat ggtcgtcgcg acggccacca cggcttttcgc    180 gcacggcaat ccgccgtacc acccgccggc cgattcgctc cgcgcgctgg ctgcgaagat     240
aggcctccgc gtcggtaccg ccatcattcc gtacgacctc gaccatccgg attacgcggc    300
aatcgccgcc agtcaattct cggtcgtcac cccaggcaac gaaatgaagt ggcaggtcgt    360
tgaaccgacc caaggtacgt acgattggtc cggcggcgat cggctcgtgc aattcgcgca    420
agaacacgga cagctcgtcc gcggccacac gctcgtctgg cacaaccagc tccccgactg    480
gctggtccag ggcgtcaaca acggtacgat ttccaacgcg caattgcggg acctgctgca    540
caagcacatc gtggacgaag tcaccccattt caaaggaaag atctggcaat gggacgtcgc    600
gaatgaattc ttcgccaact cctgggaccc gcatccactc cccgacggca tcaacggaga    660
cgatttctgg gtgcagcatc tcggtgaggg aatcatcgcc gacgccttcc gctgggcgca    720
ccaggccgat ccgcacgcgc tgttgttcta caacgactac aacatcgccg gcgaagacgg    780
cacgaacgcc aaggccgacg cggtgtacaa ctgggtgaag aagatgctcg ccgagggtgt    840
gccgatcaac ggcatcggtg accagggtca cctggacacc cagtacggct tcccgacaaa    900
gatgcaggag gacttgcagc ggtacgccga cttgggtctg aaggtggcga tcaccgaagc    960
ggatgtccgc acctttgtca cggacgcgac aacgcagcaa ccgaccgacc cgctcgcgcc   1020
gtacgcgcag gcgaactact acgacgggat gctcaaggcc tgcctcgccg tcaagaactg   1080
catctcctac acggtctggg gattcgggga cgcggattcg tggattcccg gattcttctc   1140
cggcgaaggg tacgcaaatc tgtacgacgt gaacctgcag ccgaagccgg cgtacacggc   1200
```

```
cttgcagcag  acccttgcgc  tcgcagccgg  cgcgccgcac  cgggcgggat  tcggtcatca    1260
cgccctgcgc  cgataagcgt  tggtaggaac  gcctgcttgg  ggcggcacgg  accgtgccgc    1320
cccaagcggt  tggggtccct  ccgccgcaat  tgtgggtttt  cgggcactat  tccgtgctca    1380
gggagaacag  gcgcaacccg  cgctcaggag  acaacgccgc  gcgtcactcc  cactcgatgg    1440
t                                                                        1441

<210> SEQ ID NO 5
<211> LENGTH: 1441
<212> TYPE: DNA
<213> ORGANISM: Acidothermus cellulolyticus

<400> SEQUENCE: 5
gccgttgtct  gtcccgtaag  aatttccgaa  aatttcggac  acggtggagg  aatgcgcaga      60
cagggcattc  ttaaaggctt  ttaaagcctg  tgccacctcc  ttacgctact  cttacgcgag     120
ctactgccgt  cgccgcgacc  cgcgacggta  ccagcagcgc  tgccggtggt  gccgaaagcg     180
cgtgccgtta  ggcggcatgg  tgggcggccg  gctaagcgag  gcgcgcgacc  gacgcttcta     240
tccggaggcg  cagccatggc  ggtagtaagg  catgctggag  ctggtaggcc  taatgcgccg     300
ttagcggcgg  tcagttaaga  gccagcagtg  gggtccgttg  ctttacttca  ccgtccagca     360
acttggctgg  gttccatgca  tgctaaccag  gccgccgcta  gccgagcacg  ttaagcgcgt     420
tcttgtgcct  gtcgagcagg  cgccggtgtg  cgagcagacc  gtgttggtcg  aggggctgac     480
cgaccaggtc  ccgcagttgt  tgccatgcta  aaggttgcgc  gttaacgccc  tggacgacgt     540
gttcgtgtag  cacctgcttc  agtgggtaaa  gtttcctttc  tagaccgtta  ccctgcagcg     600
cttacttaag  aagcggttga  ggaccctggg  cgtaggtgag  gggctgccgt  agttgcctct     660
gctaaagacc  cacgtcgtag  agccactccc  ttagtagcgg  ctgcggaagg  cgacccgcgt     720
ggtccggcta  ggcgtgcgcg  acaacaagat  gttgctgatg  ttgtagcggc  cgcttctgcc     780
gtgcttgcgg  ttccggctgc  gccacatgtt  gacccacttc  ttctacgagc  ggctcccaca     840
cggctagttg  ccgtagccac  tggtcccagt  ggacctgtgg  gtcatgccga  agggctgttt     900
ctacgtcctc  ctgaacgtcg  ccatgcggct  gaacccagac  ttccaccgct  agtggcttcg     960
cctacaggcg  tggaaacagt  gcctgcgctg  ttgcgtcgtt  ggctggctgg  gcgagcgcgg    1020
catgcgcgtc  cgcttgatga  tgctgcccta  cgagttccgg  acggagcggc  agttcttgac    1080
gtagaggatg  tgccagaccc  ctaagcccct  gcgcctaagc  acctaagggc  ctaagaagag    1140
gccgcttccc  atgcgtttag  acatgctgca  cttggacgtc  ggcttcggcc  gcatgtgccg    1200
gaacgtcgtc  tgggaacgcg  agcgtcggcc  gcgcggcgtg  gcccgcccta  agccagtagt    1260
gcgggacgcg  gctattcgca  accatccttg  cggacgaacc  ccgccgtgcc  tggcacggcg    1320
gggttcgcca  accccaggga  ggcggcgtta  acacccaaaa  gcccgtgata  aggcacgagt    1380
ccctcttgtc  cgcgttgggc  gcgagtcctc  tgttgcggcg  cgcagtgagg  gtgagctacc    1440
a                                                                        1441

<210> SEQ ID NO 6
<211> LENGTH: 14
<212> TYPE: PRT
<213> ORGANISM: Acidothermus cellulolyticus

<400> SEQUENCE: 6

His Gly Asn Pro Pro Tyr His Pro Pro Ala Asp Ser Leu Arg
  1               5                  10
```

<210> SEQ ID NO 7
<211> LENGTH: 18
<212> TYPE: PRT
<213> ORGANISM: Acidothermus cellulolyticus

<400> SEQUENCE: 7

Trp Gln Val Val Glu Pro Thr Gln Gly Thr Tyr Asp Trp Ser Gly Gly
 1               5                  10                  15

Asp Arg

<210> SEQ ID NO 8
<211> LENGTH: 13
<212> TYPE: PRT
<213> ORGANISM: Acidothermus cellulolyticus

<400> SEQUENCE: 8

Leu Val Gln Phe Ala Gln Glu His Gly Gln Leu Val Arg
 1               5                  10

<210> SEQ ID NO 9
<211> LENGTH: 10
<212> TYPE: PRT
<213> ORGANISM: Acidothermus cellulolyticus

<400> SEQUENCE: 9

His Ile Val Asp Glu Val Thr His Phe Lys
 1               5                  10

<210> SEQ ID NO 10
<211> LENGTH: 19
<212> TYPE: PRT
<213> ORGANISM: Acidothermus cellulolyticus

<400> SEQUENCE: 10

Pro Ala Tyr Thr Ala Leu Gln Gln Thr Leu Ala Leu Ala Ala Gly Ala
 1               5                  10                  15

Pro His Arg

<210> SEQ ID NO 11
<211> LENGTH: 9
<212> TYPE: DNA
<213> ORGANISM: Acidothermus cellulolyticus

<400> SEQUENCE: 11 gaaactttc                                                                9

<210> SEQ ID NO 12
<211> LENGTH: 9
<212> TYPE: DNA
<213> ORGANISM: Acidothermus cellulolyticus

<400> SEQUENCE: 12 tttccgaaa                                                                9

<210> SEQ ID NO 13
<211> LENGTH: 15
<212> TYPE: DNA
<213> ORGANISM: Acidothermus cellulolyticus

<400> SEQUENCE: 13
tccgaaaatt tcgga                                                        15

```
<210> SEQ ID NO 14
<211> LENGTH: 32
<212> TYPE: DNA
<213> ORGANISM: Artificial Sequence
<220> FEATURE:
<223> OTHER INFORMATION: Synthesized Construct

<400> SEQUENCE: 14
gtggtggagc tcgcaattcg ttcacgttga gg                                        32

<210> SEQ ID NO 15
<211> LENGTH: 32
<212> TYPE: DNA
<213> ORGANISM: Artificial Sequence
<220> FEATURE:
<223> OTHER INFORMATION: Synthesized Construct

<400> SEQUENCE: 15
gtggtgtcta gaaccatcga gtgggagtga cg                                        32

<210> SEQ ID NO 16
<211> LENGTH: 21
<212> TYPE: DNA
<213> ORGANISM: Artificial Sequence
<220> FEATURE:
<223> OTHER INFORMATION: Synthesized Construct

<400> SEQUENCE: 16
caaaggaaag atctggcaat g                                                    21

<210> SEQ ID NO 17
<211> LENGTH: 21
<212> TYPE: DNA
<213> ORGANISM: Artificial Sequence
<220> FEATURE:
<223> OTHER INFORMATION: Synthesized Construct

<400> SEQUENCE: 17
tgagcatccc gtcgtagtag t                                                    21

<210> SEQ ID NO 18
<211> LENGTH: 21
<212> TYPE: DNA
<213> ORGANISM: Artificial Sequence
<220> FEATURE:
<223> OTHER INFORMATION: Synthesized Construct

<400> SEQUENCE: 18
gacccgaccg aggtttatta c                                                    21

<210> SEQ ID NO 19
<211> LENGTH: 21
<212> TYPE: DNA
<213> ORGANISM: Artificial Sequence
<220> FEATURE:
<223> OTHER INFORMATION: Synthesized Construct

<400> SEQUENCE: 19
gccgaacttg ttcaccaaat a                                                    21

<210> SEQ ID NO 20
<211> LENGTH: 6
<212> TYPE: DNA
<213> ORGANISM: Acidothermus cellulolyticus

<400> SEQUENCE: 20
```

```
tggagg                                                                6
```

<210> SEQ ID NO 21
<211> LENGTH: 6
<212> TYPE: DNA
<213> ORGANISM: Acidothermus cellulolyticus

<400> SEQUENCE: 21

```
cctcct                                                                6
```

<210> SEQ ID NO 22
<211> LENGTH: 11
<212> TYPE: PRT
<213> ORGANISM: Acidothermus cellulolyticus

<400> SEQUENCE: 22

```
His Gly Asn Pro Pro Tyr His Pro Pro Ala Asp
 1               5                  10
```

<210> SEQ ID NO 23
<211> LENGTH: 5
<212> TYPE: PRT
<213> ORGANISM: Acidothermus cellulolyticus

<400> SEQUENCE: 23

```
Asp Val Val Asn Glu
 1               5
```

<210> SEQ ID NO 24
<211> LENGTH: 4
<212> TYPE: PRT
<213> ORGANISM: Acidothermus cellulolyticus

<400> SEQUENCE: 24

```
Thr Glu Leu Asp
 1
```

<210> SEQ ID NO 25
<211> LENGTH: 5
<212> TYPE: PRT
<213> ORGANISM: Acidothermus cellulolyticus

<400> SEQUENCE: 25

```
Asp Val Ala Asn Glu
 1               5
```

<210> SEQ ID NO 26
<211> LENGTH: 4
<212> TYPE: PRT
<213> ORGANISM: Acidothermus cellulolyticus

<400> SEQUENCE: 26

```
Thr Glu Ala Asp
 1
```

<210> SEQ ID NO 27
<211> LENGTH: 5
<212> TYPE: PRT
<213> ORGANISM: Acidothermus cellulolyticus

<400> SEQUENCE: 27

```
Pro His Pro Leu Pro
 1               5
```

<210> SEQ ID NO 28
<211> LENGTH: 295
<212> TYPE: PRT
<213> ORGANISM: Acidothermus cellulolyticus

<400> SEQUENCE: 28

```
Ala Ala Ser Gln Phe Ser Val Val Thr Pro Gly Asn Glu Met Lys Trp
  1               5                  10                  15

Gln Val Val Glu Pro Thr Gln Gly Thr Tyr Asp Trp Ser Gly Gly Asp
             20                  25                  30

Arg Leu Val Gln Phe Ala Gln Glu His Gly Gln Leu Val Arg Gly His
         35                  40                  45

Thr Leu Val Trp His Asn Gln Leu Pro Asp Trp Leu Val Gln Gly Val
 50                  55                  60

Asn Asn Gly Thr Ile Ser Asn Ala Gln Leu Arg Asp Leu Leu His Lys
 65                  70                  75                  80

His Ile Val Asp Glu Val Thr His Phe Lys Gly Lys Ile Trp Gln Trp
                 85                  90                  95

Asp Val Ala Asn Glu Phe Phe Ala Asn Ser Trp Asp Pro His Pro Leu
            100                 105                 110

Pro Asp Gly Ile Asn Gly Asp Asp Phe Trp Val Gln His Leu Gly Glu
        115                 120                 125

Gly Ile Ile Ala Asp Ala Phe Arg Trp Ala His Gln Ala Asp Pro His
130                 135                 140

Ala Leu Leu Phe Tyr Asn Asp Tyr Asn Ile Ala Gly Glu Asp Gly Thr
145                 150                 155                 160

Asn Ala Lys Ala Asp Ala Val Tyr Asn Trp Val Lys Lys Met Leu Ala
                165                 170                 175

Glu Gly Val Pro Ile Asn Gly Ile Gly Asp Gln Gly His Leu Asp Thr
            180                 185                 190

Gln Tyr Gly Phe Pro Thr Lys Met Gln Glu Asp Leu Gln Arg Tyr Ala
        195                 200                 205

Asp Leu Gly Leu Lys Val Ala Ile Thr Glu Ala Asp Val Arg Thr Phe
    210                 215                 220

Val Thr Asp Ala Thr Thr Gln Gln Pro Thr Asp Pro Leu Ala Pro Tyr
225                 230                 235                 240

Ala Gln Ala Asn Tyr Tyr Asp Gly Met Leu Lys Ala Cys Leu Ala Val
                245                 250                 255

Lys Asn Cys Ile Ser Tyr Thr Val Trp Gly Phe Gly Asp Ala Asp Ser
            260                 265                 270

Trp Ile Pro Gly Phe Phe Ser Gly Glu Gly Tyr Ala Asn Leu Tyr Asp
        275                 280                 285

Val Asn Leu Gln Pro Lys Pro
    290                 295
```

<210> SEQ ID NO 29
<211> LENGTH: 290
<212> TYPE: PRT
<213> ORGANISM: Catenulispora acidiphila

<400> SEQUENCE: 29

```
Ala Ala Thr Gln Phe Ser Val Val Thr Pro Gly Asn Glu Met Lys Trp
  1               5                  10                  15

Gln Val Val Glu Pro Thr Gln Gly Thr Tyr Asp Trp Ser Gly Gly Asp
             20                  25                  30
```

Arg Leu Val Gln Phe Ala Gln Gln Asn His Gln Leu Val Arg Gly His
                35                  40                  45

Val Leu Leu Trp His Asn Gln Leu Pro Asp Trp Leu Thr Thr Gly Val
 50                  55                  60

Thr Asn Gly Thr Ile Ser Asp Ala Gln Leu Arg Asp Leu Leu His Lys
 65                  70                  75                  80

His Ile Thr Asp Glu Val Thr His Phe Lys Gly Lys Ile Trp Gln Trp
                 85                  90                  95

Asp Val Ala Asn Glu Phe Phe Thr Asp Asp Pro Ser Gln Leu Asn
                100                 105                 110

Pro Asn Asp Phe Trp Ile Ser His Leu Gly Thr Gly Val Ile Ala Asp
                115                 120                 125

Ala Phe Arg Trp Ala His Ala Ala Asp Pro Lys Ala Leu Leu Phe Tyr
            130                 135                 140

Asn Asp Tyr Asn Ile Ala Gly Glu Asp Gly Thr Asn Ala Lys Ser Asp
145                 150                 155                 160

Ala Ala Tyr Thr Phe Ile Lys Gln Leu Val Ala Gln Gly Val Pro Ile
                165                 170                 175

Ser Gly Val Gly Asp Gln Gly His Leu Asp Thr Gln Tyr Gly Phe Pro
            180                 185                 190

Thr Lys Met Thr Asp Asp Leu Gln Arg Phe Ala Asn Leu Gly Leu Lys
            195                 200                 205

Thr Ala Ile Thr Glu Ala Asp Val Arg Thr Phe Val Asp Ser Pro Thr
210                 215                 220

Thr Gln Val Pro Thr Asp His Leu Ala Thr Phe Ala Gln Pro Tyr Glu
225                 230                 235                 240

Tyr Ser Gln Met Leu Gln Ala Cys Leu Ala Val Lys Gln Cys Ile Ser
                245                 250                 255

Phe Thr Val Trp Gly Phe Gly Asp Thr Asp Ser Trp Ile Pro Gly Trp
            260                 265                 270

Phe Thr Asn Glu Gly Tyr Ala Asn Leu Tyr Asp Val Asn Leu Ala Pro
            275                 280                 285

Lys Pro
    290

<210> SEQ ID NO 30
<211> LENGTH: 274
<212> TYPE: PRT
<213> ORGANISM: Cellulosimicrobium sp. HY-12

<400> SEQUENCE: 30

Ala Gly Glu Gln Phe Ser Thr Val Ser Pro Glu Asn Val Met Lys Trp
 1               5                  10                  15

Asp Thr Ile Glu Pro Thr Gln Gly Thr Tyr Asn Phe Ala Pro Ala Asp
                20                  25                  30

Lys Leu Val Ala Phe Ala Gln Gln His Gly Gln Leu Val Arg Gly His
                35                  40                  45

Thr Leu Val Trp His Asn Gln Leu Pro Ser Trp Leu Thr Ala Glu Ala
 50                  55                  60

Asp Ser Leu Thr Ala Asp Gln Leu Arg Ala Ile Leu Lys Lys His Ile
 65                  70                  75                  80

Gln Thr Glu Val Lys His Phe Lys Gly Lys Ile Trp Gln Trp Asp Val
                 85                  90                  95

Val Asn Glu Ala Phe Ala Asp Asp Gly Thr Leu Arg Asp Asp Ile Trp
                100                 105                 110

```
Ser Gln Lys Leu Gly Asp Ser Tyr Ile Ala Asp Ala Phe Arg Trp Ala
            115                 120                 125

His Glu Ala Asp Pro Lys Ala Lys Leu Phe Tyr Asn Asp Tyr Asn Ile
130                 135                 140

Glu Tyr Thr Gly Ala Lys Ser Glu Ala Val Tyr Ala Met Val Lys Lys
145                 150                 155                 160

Leu Gln Ala Gln Gly Val Pro Ile Asp Gly Val Gly Phe Gln Asp His
                165                 170                 175

Leu Asp Thr Gln Tyr Gly Thr Pro Asn Leu Gln Glu Thr Met Gln Lys
            180                 185                 190

Phe Ala Asp Leu Gly Leu Asp Thr Ala Val Thr Glu Ala Asp Val Arg
            195                 200                 205

Thr Thr Leu Pro Val Thr Thr Val Glu Gln Ala Gln Asn Ser Met
210                 215                 220

Trp Ser Gln Ser Leu Ser Ala Cys Leu Leu Val Lys Arg Cys Ile Ser
225                 230                 235                 240

Phe Thr Val Trp Gly Ile Asp Asp Gly Ser Ser Trp Val Pro Ser Thr
                245                 250                 255

Phe Glu Gly Glu Gly Ala Ala Leu Leu Trp Asp Asp Asp Phe Gln Pro
            260                 265                 270

Lys Ala

<210> SEQ ID NO 31
<211> LENGTH: 261
<212> TYPE: PRT
<213> ORGANISM: Cellulomonas fimi

<400> SEQUENCE: 31

Ala Asn Arg Glu Phe Asn Met Ile Thr Ala Glu Asn Glu Met Lys Met
  1               5                  10                  15

Asp Ala Thr Glu Pro Ser Gln Gly Arg Phe Thr Phe Thr Asn Gly Asp
             20                  25                  30

Arg Ile Val Asn Trp Ala Leu Ser Asn Gly Lys Arg Val Arg Gly His
             35                  40                  45

Thr Leu Ala Trp His Ala Gln Gln Pro Gly Trp Met Gln Ser Met Ser
 50                  55                  60

Gly Ser Ala Leu Arg Asn Ala Leu Ile Asn His Val Thr Gln Val Ala
 65                  70                  75                  80

Ser Tyr Tyr Arg Gly Lys Val Tyr Ala Trp Asp Val Val Asn Glu Ala
             85                  90                  95

Phe Ala Asp Asp Gly Arg Gly Ser Arg Arg Asp Ser Asn Leu Gln Arg
            100                 105                 110

Thr Gly Asn Asp Trp Ile Glu Ala Ala Phe Arg Ala Ala Arg Ala Ala
            115                 120                 125

Asp Pro Asn Ala Lys Leu Cys Tyr Asn Asp Tyr Asn Thr Asp Asn Trp
130                 135                 140

Ser His Ala Lys Thr Gln Gly Val Tyr Asn Met Val Lys Asp Phe Lys
145                 150                 155                 160

Ala Arg Gly Val Pro Ile Asp Cys Val Gly Phe Gln Ala His Phe Asn
            165                 170                 175

Ser Gly Asn Pro Val Pro Ser Asn Tyr His Thr Thr Leu Gln Asn Phe
            180                 185                 190

Ala Asp Leu Gly Val Asp Val Gln Ile Thr Glu Leu Asp Ile Glu Gly
            195                 200                 205
```

```
Ser Gly Ser Ser Gln Ala Gln Gln Tyr Gln Gly Val Gln Ala Cys
        210                 215                 220

Leu Ala Val Ser Arg Cys Thr Gly Ile Thr Val Trp Gly Val Arg Asp
225                 230                 235                 240

Thr Asp Ser Trp Arg Ala Ser Gly Thr Pro Leu Leu Phe Asp Gly Ser
                245                 250                 255

Gly Asn Lys Lys Ala
            260

<210> SEQ ID NO 32
<211> LENGTH: 258
<212> TYPE: PRT
<213> ORGANISM: Streptomyces thermoviolaceus

<400> SEQUENCE: 32

Ala Ser Arg Glu Phe Asn Met Val Thr Ala Glu Asn Glu Met Lys Ile
1               5                   10                  15

Asp Ala Thr Glu Pro Gln Arg Gly Gln Phe Asp Phe Ser Ala Gly Asp
                20                  25                  30

Arg Val Tyr Asn Trp Ala Val Gln Asn Gly Lys Glu Val Arg Gly His
            35                  40                  45

Thr Leu Ala Trp His Ser Gln Gln Pro Tyr Trp Met Gln Ser Leu Ser
    50                  55                  60

Gly Ser Asp Leu Arg Gln Ala Met Ile Asp His Ile Asn Gly Val Met
65                  70                  75                  80

Asn His Tyr Lys Gly Lys Ile Ala Gln Trp Asp Val Val Asn Glu Ala
                85                  90                  95

Phe Glu Asp Gly Asn Ser Gly Ala Arg Arg Asp Ser Asn Leu Gln Arg
                100                 105                 110

Thr Gly Asn Asp Trp Ile Glu Val Ala Phe Arg Thr Ala Arg Ala Ala
            115                 120                 125

Asp Pro Ser Ala Lys Leu Cys Tyr Asn Asp Tyr Asn Ile Glu Asn Trp
        130                 135                 140

Thr Trp Ala Lys Thr Gln Ala Val Tyr Asn Met Val Arg Asp Phe Lys
145                 150                 155                 160

Gln Arg Gly Val Pro Ile Asp Cys Val Gly Phe Gln Ser His Phe Asn
                165                 170                 175

Ser Gly Ser Pro Tyr Asp Ser Asn Phe Arg Thr Thr Leu Gln Ser Phe
            180                 185                 190

Ala Ala Leu Gly Val Asp Val Ala Ile Thr Glu Leu Asp Ile Gln Gly
        195                 200                 205

Ala Ser Pro Thr Thr Tyr Ala Asn Val Val Asn Asp Cys Leu Ala Val
    210                 215                 220

Ser Arg Cys Leu Gly Ile Thr Val Trp Gly Val Arg Asp Thr Asp Ser
225                 230                 235                 240

Trp Arg Ser Gly Asp Thr Pro Leu Leu Phe Asn Gly Asp Gly Ser Lys
                245                 250                 255

Lys Pro

<210> SEQ ID NO 33
<211> LENGTH: 257
<212> TYPE: PRT
<213> ORGANISM: Thermoascus aurantiacus

<400> SEQUENCE: 33
```

```
Ile Gln Ala Asp Phe Gly Gln Val Thr Pro Glu Asn Ser Met Lys Trp
  1               5                  10                  15

Asp Ala Thr Glu Pro Ser Gln Gly Asn Phe Asn Phe Ala Gly Ala Asp
             20                  25                  30

Tyr Leu Val Asn Trp Ala Gln Gln Asn Gly Lys Leu Ile Arg Gly His
         35                  40                  45

Thr Leu Val Trp His Ser Gln Leu Pro Ser Trp Val Ser Ser Ile Thr
 50                  55                  60

Asp Lys Asn Thr Leu Thr Asn Val Met Lys Asn His Ile Thr Thr Leu
 65                  70                  75                  80

Met Thr Arg Tyr Lys Gly Lys Ile Arg Ala Trp Asp Val Val Asn Glu
                 85                  90                  95

Ala Phe Asn Glu Asp Gly Ser Leu Arg Gln Thr Val Phe Leu Asn Val
            100                 105                 110

Ile Gly Glu Asp Tyr Ile Pro Ile Ala Phe Gln Thr Ala Arg Ala Ala
            115                 120                 125

Asp Pro Asn Ala Lys Leu Tyr Ile Asn Asp Tyr Asn Leu Asp Ser Ala
        130                 135                 140

Ser Tyr Pro Lys Thr Gln Ala Ile Val Asn Arg Val Lys Gln Trp Arg
145                 150                 155                 160

Ala Ala Gly Val Pro Ile Asp Gly Ile Gly Ser Gln Thr His Leu Ser
                165                 170                 175

Ala Gly Gln Gly Ala Gly Val Leu Gln Ala Leu Pro Leu Leu Ala Ser
            180                 185                 190

Ala Gly Thr Pro Glu Val Ala Ile Thr Glu Leu Asp Val Ala Gly Ala
            195                 200                 205

Ser Pro Thr Asp Tyr Val Asn Val Val Asn Ala Cys Leu Asn Val Gln
        210                 215                 220

Ser Cys Val Gly Ile Thr Val Trp Gly Val Ala Asp Pro Asp Ser Trp
225                 230                 235                 240

Arg Ala Ser Thr Thr Pro Leu Leu Phe Asp Gly Asn Phe Asn Pro Lys
                245                 250                 255

Pro

<210> SEQ ID NO 34
<211> LENGTH: 275
<212> TYPE: PRT
<213> ORGANISM: Phanerochaete chrysosporium

<400> SEQUENCE: 34

Leu Asp Asp Asn Thr Met Phe Gly Gln Ile Thr Pro Ala Asn Ser Met
  1               5                  10                  15

Lys Trp Asp Ala Thr Glu Pro Gln Gly Val Phe Thr Phe Ser Gly
             20                  25                  30

Gly Asp Gln Ile Ala Thr Leu Ala Lys Thr Asn Gly Met Leu Leu Arg
         35                  40                  45

Gly His Asn Cys Val Trp Tyr Asn Gln Leu Pro Ser Trp Val Ser Ser
 50                  55                  60

Gly Ser Phe Thr Ala Ala Gln Leu Thr Ser Ile Ile Gln Asn His Cys
 65                  70                  75                  80

Ser Thr Leu Val Thr His Tyr Lys Gly Gln Val Tyr Ala Trp Asp Val
                 85                  90                  95

Val Asn Glu Pro Phe Asn Asp Asp Gly Thr Trp Arg Thr Asp Val Phe
            100                 105                 110
```

Tyr Asn Thr Leu Gly Thr Ser Tyr Val Gln Ile Ala Leu Glu Ala Ala
                115                 120                 125

Arg Ala Ala Asp Pro Asn Ala Lys Leu Tyr Ile Asn Glu Tyr Asn Ile
        130                 135                 140

Glu Phe Ala Gly Ala Lys Ala Thr Ser Leu Leu Asn Leu Val Lys Ser
145                 150                 155                 160

Leu Lys Ala Ala Asp Val Pro Leu Asp Gly Ile Gly Phe Gln Cys His
                165                 170                 175

Leu Ile Val Gly Glu Phe Ser Gly Pro Gly Leu Gln Thr Gln Leu Ser
                180                 185                 190

Thr Phe Ala Ala Gln Gly Val Glu Val Ala Ile Thr Glu Leu Asp Ile
                195                 200                 205

Arg Met Thr Leu Pro Ser Thr Pro Ala Leu Leu Ala Gln Gln Gln Thr
        210                 215                 220

Asp Tyr Asn Ser Val Ile Thr Ala Cys Met Asn Val Glu Ser Cys Ile
225                 230                 235                 240

Gly Val Thr Val Trp Asp Trp Thr Asp Lys Tyr Ser Trp Val Pro Asn
                245                 250                 255

Thr Phe Ser Gly Gln Gly Ala Ala Cys Pro Trp Asp Gln Asn Phe Val
                260                 265                 270

Lys Lys Pro
        275

<210> SEQ ID NO 35
<211> LENGTH: 272
<212> TYPE: PRT
<213> ORGANISM: Thermobifida alba

<400> SEQUENCE: 35

Ala Ala Thr Gln Phe Ser Ala Ile Thr His Glu Asn Glu Met Lys Trp
1               5                   10                  15

Glu Ser Leu Glu Pro Gln Arg Gly Gln Tyr Asn Trp Ser Gln Ala Asp
                20                  25                  30

Asn Ile Ile Asn Phe Ala Lys Ala Asn Asn Gln Ile Val Arg Gly His
                35                  40                  45

Thr Leu Val Trp His Ser Gln Leu Pro Ser Trp Leu Asn Asn Gly Gly
        50                  55                  60

Phe Ser Gly Ser Gln Leu Arg Ser Ile Met Glu Asn His Ile Glu Val
65                  70                  75                  80

Val Ala Gly Arg Tyr Arg Gly Asp Val Tyr Ala Trp Asp Val Val Asn
                85                  90                  95

Glu Ala Phe Asn Glu Asp Gly Thr Leu Arg Asp Ser Ile Trp Tyr Arg
                100                 105                 110

Gly Met Gly Arg Asp Tyr Ile Ala His Ala Phe Arg Lys Ala His Glu
                115                 120                 125

Val Asp Pro Asp Ala Lys Leu Tyr Ile Asn Asp Tyr Asn Ile Glu Gly
        130                 135                 140

Ile Asn Ala Lys Ser Asn Gly Leu Tyr Asn Leu Val Asp Leu Leu
145                 150                 155                 160

Arg Asp Gly Val Pro Ile His Gly Ile Gly Ile Gln Ser His Leu Ile
                165                 170                 175

Val Gly Gln Val Pro Ser Thr Phe Gln Gln Asn Ile Gln Arg Phe Ala
                180                 185                 190

Asp Leu Gly Leu Asp Val Ala Ile Thr Glu Leu Asp Ile Arg Met Gln
                195                 200                 205

Met Pro Ala Asp Gln Tyr Lys Leu Gln Gln Ala Arg Asp Tyr Glu
210                 215                 220

Ala Val Val Asn Ala Cys Leu Ala Val Thr Arg Cys Ile Gly Ile Thr
225                 230                 235                 240

Val Trp Gly Ile Asp Asp Glu Arg Ser Trp Val Pro Tyr Thr Phe Pro
            245                 250                 255

Gly Glu Gly Ala Pro Leu Leu Tyr Asp Gly Tyr Asn Arg Lys Pro
        260                 265                 270

<210> SEQ ID NO 36
<211> LENGTH: 272
<212> TYPE: PRT
<213> ORGANISM: Streptomyces avermitilis

<400> SEQUENCE: 36

Leu Asp Arg Glu Phe Asn Ser Val Thr Ala Glu Asn Ala Met Lys Trp
1               5                   10                  15

Asp Ala Val Glu Pro Ser Arg Gly Gly Phe Asp Trp Ala Ala Ala Asp
                20                  25                  30

Arg Leu Val Ala His Ala Ser Ala His Gly Gln Gly Val Arg Gly His
            35                  40                  45

Thr Leu Ala Trp Tyr Ala Gln Leu Pro Ser Trp Leu Lys Asn Gly Asn
50                  55                  60

Phe Ser Ala Ser Glu Leu Asn Thr Ile Leu Lys Ser His Ile Asp Thr
65                  70                  75                  80

Glu Val Gly Arg Tyr Lys Gly Lys Val Tyr Ala Trp Asp Val Val Asn
                85                  90                  95

Glu Thr Phe Asn Glu Asp Gly Ser Met Arg Gly Ser Leu Trp Gln Asp
                100                 105                 110

Lys Leu Gly Thr Gly Tyr Ile Ala Asn Ala Leu Arg Trp Ala His Ala
            115                 120                 125

Ala Asp Pro Ala Ala Lys Leu Tyr Ile Asn Asp Tyr Asn Ile Glu Ala
        130                 135                 140

Asp Asn Ala Lys Ser Asp Ala Leu Tyr Ala Leu Ala Lys Gln Leu Leu
145                 150                 155                 160

Ala Asp Gly Val Pro Leu His Gly Ile Gly Phe Gln Ser His Phe Val
                165                 170                 175

Val Gly Gln Val Pro Ser Thr Met Lys Ala Asn Leu Lys Arg Phe Ser
            180                 185                 190

Asp Leu Gly Leu Glu Val Ser Val Thr Glu Leu Asp Ile Arg Ile Pro
        195                 200                 205

Leu Pro Ala Ser Ser Asp Glu Leu Ala Gln Gln Ser Ala Asp Tyr Lys
210                 215                 220

Thr Ala Ser Glu Asn Cys Leu Gly Val Ala Arg Cys Ala Gly Ile Thr
225                 230                 235                 240

Val Trp Gly Val Ser Asp Lys Tyr Ser Trp Ile Pro Gly Thr Phe Ser
            245                 250                 255

Gly Tyr Gly Ala Ala Leu Pro Tyr Asn Glu Ser Tyr Ala Ala Lys Pro
        260                 265                 270

<210> SEQ ID NO 37
<211> LENGTH: 276
<212> TYPE: PRT
<213> ORGANISM: Cryptococcus adeliensis

<400> SEQUENCE: 37

-continued

```
Leu Glu Ser Gln Phe Asp Ala Ile Thr Pro Glu Asn Glu Met Lys Trp
 1               5                  10                  15

Glu Val Ile Glu Pro Thr Glu Gly Asn Phe Asp Phe Ser Gly Thr Asp
            20                  25                  30

Lys Ile Ile Ala Glu Ala Lys Lys Thr Gly Ser Leu Val Arg Gly His
        35                  40                  45

Asn Ile Cys Trp Asp Ser Gln Thr Pro Ser Trp Val Thr Ser Ile Thr
 50                  55                  60

Asp Pro Thr Arg Leu Lys Gln Val Leu Lys Asn His Ile Gln Gly Val
 65                  70                  75                  80

Ile Gly Arg Tyr Lys Asp Leu Glu Tyr Phe Asp Ile Val Asn Glu
                85                  90                  95

Pro Ile Asn Glu Asn Gly Thr Tyr Lys Ser Asn Val Trp Tyr Asn Val
            100                 105                 110

Leu Gly Glu Ser Tyr Ile Glu Thr Ala Leu Arg Tyr Ala His Glu Val
            115                 120                 125

Ala Pro Lys Met Lys Leu Cys Ile Asn Glu Tyr Asn Ile Glu Thr Val
        130                 135                 140

Asn Ala Lys Ser Lys Ser Met Ala Glu Ile Ala Arg Lys Leu Leu Ala
145                 150                 155                 160

Lys Gly Ala Pro Leu His Cys Ile Gly Leu Glu Ser His Phe Ile Gly
                165                 170                 175

Gly Ser Thr Pro Arg Asp Ile Pro Ala Ala Met Asn Leu Phe Ser Asp
            180                 185                 190

Gln Gly Leu Glu Val Pro Met Thr Glu Leu Asp Ile Arg Ile Pro Val
        195                 200                 205

Asn Ala Asn Asp Gln Ala Val Asn Ala Ser Ile Ala Lys Thr Gln Ala
210                 215                 220

Asp Glu Tyr Tyr Leu Ser Ile Asn Ala Cys Leu Gly Asn Ser Leu Cys
225                 230                 235                 240

Pro Gly Val Ser Ile Trp Gln Phe Ala Asp Pro Thr Ser Trp Ile Pro
                245                 250                 255

Gly Val Phe Pro Gly Thr Gly Ala Ala Leu Ile Tyr Asp Ala Glu Tyr
            260                 265                 270

Gln Pro Lys Ser
        275

<210> SEQ ID NO 38
<211> LENGTH: 291
<212> TYPE: PRT
<213> ORGANISM: Unknown
<220> FEATURE:
<223> OTHER INFORMATION: Uncultured bacterium

<400> SEQUENCE: 38

Leu Lys Lys His Phe Asn Ser Leu Thr Pro Glu Asn Gln Met Lys Trp
 1               5                  10                  15

Glu Ile Ile His Pro Thr Pro Ser Thr Tyr Arg Phe Glu Pro Ala Asp
            20                  25                  30

Lys Ile Val Glu Phe Ala Met Glu Asn Lys Met Arg Val Arg Gly His
        35                  40                  45

Thr Leu Val Trp His Gln Gln Val Pro Ala Trp Val Phe Arg Asp Asp
 50                  55                  60

Asn Gly Asn Pro Val Ser Lys Glu Val Leu Leu Gln Arg Leu Lys Glu
 65                  70                  75                  80
```

His Ile Met Lys Val Gly Tyr Tyr Lys Gly Lys Val Ala Val Trp
            85                  90                  95

Asp Val Val Asn Glu Ala Ile Ser Asp Asn Pro Ser Glu Phe Leu Arg
            100                 105                 110

Asp Ala Pro Trp Tyr Lys Ile Gly Gly Glu Val Ile Glu Lys Ala
            115                 120                 125

Phe Ile Trp Ala His Glu Ala Asp Pro Asn Ala Leu Leu Phe Tyr Asn
130                 135                 140

Asp Tyr Asn Leu Glu Glu Pro Ile Lys Arg Asp Lys Ala Tyr Gln Leu
145                 150                 155                 160

Val Lys Lys Leu Lys Glu Lys Gly Ile Pro Ile His Gly Val Gly Ile
                165                 170                 175

Gln Gly His Trp Leu Leu Gln Trp Pro Thr Pro Glu Met Leu Glu Glu
            180                 185                 190

Ser Ile Lys Lys Phe Ala Ser Leu Gly Val Lys Val Glu Ile Thr Glu
            195                 200                 205

Leu Asp Val Ser Ile Tyr Arg Asp Arg Tyr Glu Asn Ala Asn Phe Ser
210                 215                 220

Lys Asn Pro Pro Gln Asp Arg Leu Glu Ile Gln Ala Gln Val Tyr Lys
225                 230                 235                 240

Arg Ile Phe Glu Val Leu Arg Arg Asn Lys Asn Tyr Val Ser Gly Val
                245                 250                 255

Thr Phe Trp Gly Val Thr Asp Gly Val Thr Trp Leu Asp Phe Trp Pro
            260                 265                 270

Val Arg Gly Arg Lys Asp Tyr Pro Leu Ile Phe Asp Ala Asn Gln Asn
            275                 280                 285

Pro Lys Lys
    290

<210> SEQ ID NO 39
<211> LENGTH: 274
<212> TYPE: PRT
<213> ORGANISM: Thermotoga maritima

<400> SEQUENCE: 39

Ala Arg Arg Glu Phe Asn Ile Leu Thr Pro Glu Asn Gln Met Lys Trp
1               5                   10                  15

Asp Thr Ile His Pro Glu Arg Asp Arg Tyr Asn Phe Thr Pro Ala Glu
            20                  25                  30

Lys His Val Glu Phe Ala Glu Glu Asn Asp Met Ile Val His Gly His
        35                  40                  45

Thr Leu Val Trp His Asn Gln Leu Pro Gly Trp Ile Thr Gly Arg Glu
    50                  55                  60

Trp Thr Lys Glu Glu Leu Leu Asn Val Leu Glu Asp His Ile Lys Thr
65                  70                  75                  80

Val Val Ser His Phe Lys Gly Arg Val Lys Ile Trp Asp Val Val Asn
                85                  90                  95

Glu Ala Val Ser Asp Ser Gly Thr Tyr Arg Glu Ser Val Trp Tyr Lys
            100                 105                 110

Thr Ile Gly Pro Glu Tyr Ile Glu Lys Ala Phe Arg Trp Ala Lys Glu
            115                 120                 125

Ala Asp Pro Asp Ala Ile Leu Ile Tyr Asn Asp Tyr Ser Ile Glu Glu
130                 135                 140

Ile Asn Ala Lys Ser Asn Phe Val Tyr Asn Met Ile Lys Glu Leu Lys

```
145                 150                 155                 160
Glu Lys Gly Val Pro Val Asp Gly Ile Gly Phe Gln Met His Ile Asp
                165                 170                 175
Tyr Arg Gly Leu Asn Tyr Asp Ser Phe Arg Arg Asn Leu Glu Arg Phe
                180                 185                 190
Ala Lys Leu Gly Leu Gln Ile Tyr Ile Thr Glu Met Asp Val Arg Ile
            195                 200                 205
Pro Leu Ser Gly Ser Glu Tyr Tyr Leu Lys Lys Gln Ala Glu Val
            210                 215                 220
Cys Ala Lys Ile Phe Asp Ile Cys Leu Asp Asn Pro Ala Val Lys Ala
225                 230                 235                 240
Ile Gln Phe Trp Gly Phe Thr Asp Lys Tyr Ser Trp Val Pro Gly Phe
                245                 250                 255
Phe Lys Gly Tyr Gly Lys Ala Leu Leu Phe Asp Glu Asn Tyr Asn Pro
                260                 265                 270
Lys Pro

<210> SEQ ID NO 40
<211> LENGTH: 9
<212> TYPE: PRT
<213> ORGANISM: Acidothermus cellulolyticus
<220> FEATURE:
<221> NAME/KEY: VARIANT
<222> LOCATION: (2)...(4)
<223> OTHER INFORMATION: Xaa = Any Amino Acid and up to 3 of them can be
      present or absent
<220> FEATURE:
<221> NAME/KEY: VARIANT
<222> LOCATION: (6)...(8)
<223> OTHER INFORMATION: Xaa = Any Amino Acid and up to 3 of them can be
      present or absent

<400> SEQUENCE: 40

Pro Xaa Xaa Xaa Pro Xaa Xaa Xaa Pro
 1               5
```

USE OF ACIDOTHERMUS CELLULOLYTICUS XYLANASE FOR HYDROLYZING LIGNOCELLULOSE

This application is a Divisional of U.S. patent application Ser. No. 12/613,398, with a filing date of Nov. 5, 2009, now abandoned, which claims the benefit under 35 USC 119(e) of U.S. Provisional Patent Application No. 61/203,528, filed Dec. 22, 2008, the disclosure of which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 514112003910SEQLIST.txt, date recorded: Oct. 12, 2012, size: 42 KB).

BACKGROUND

1. Field

The present disclosure relates to xylanases and methods for their expression and use. Specifically, the disclosure is related to a thermophilic xylanase (Xyl-1) and homologs thereof derived from *Acidothermus cellulolyticus*, and the use of these enzymes in hydrolyzing lignocellulose.

2. Related Art

Lignocellulose is plant biomass composed of cellulose, hemicellulose, and lignin. Lignocellulose serves as an abundant and inexpensive source of fermentable biomass. However, one barrier to the utilization of lignocellulose is the tight crosslinking of the cellulose and hemicellulose to the lignin. Breaking down lignocellulose (i.e. separating cellulose and hemicellulose from lignin) is energy intensive, and thus inefficient. Efficient utilization of lignocellulosic biomass will enhance the economic competitiveness of bioconversion processes which must compete with petrochemical processes. It has been shown that xylanase enzymes can be used to efficiently break down lignocellulose.

Xylanase enzymes are important in a wide variety of biotechnological and industrial applications. These include prebleaching of kraft pulp in the pulp and paper industry, recovery of cellulose fiber in textiles, enhancing digestibility of animal feed and silage, clarification of juices and beer, separation of cereal gluten and starch, assorted applications in the bakery industry, as well as the production of xylo-oligosaccharides for pharmacological applications and food additives (1, 2, 9, 14, and 21). Furthermore, recent interest in biofuels production from lignocellulosic plant biomass has brought xylanases into renewed prominence (5). Collins et al. (4) recently reviewed the physicochemical and functional characteristics of xylanases from six different families, their mechanism of action, and industrial applications.

Xylanase production is commonly obtained from *Trichoderma reesei* and *Trichoderma harzianum* strain E58, both from the Forintek Canada Corp. culture collection. Although both fungi are prolific producers of extracellular xylanases, fungal growth and enzyme production can only be carried out at mesophilic temperatures (e.g., 28° C.). Consequently the fermentation requires considerable cooling water during fungal growth and is easily subjected to bacterial contamination. The xylanase enzymes produced are also thermally unstable, losing over 90% of their activities within a half hour of incubation at 50° C. As a result, enzymatic hydrolysis of lignocellulose using these enzymes has to be carried out at a lower temperature of about 37-45° C. This in turn lowers the hydrolysis efficiencies, necessitates aseptic conditions during hydrolysis, as well as preventing prolonged enzyme use without replacement. However, higher efficiency of hydrolysis can be obtained by using thermophilic xylanases.

Recently, several thermophilic xylanases from fungal and bacterial microorganisms have been identified (FIG. 1). For example, U.S. Pat. No. 5,935,836 discloses a thermophilic xylanase isolated from *Actinomadura flexuosa* that has an optimal pH of 6.0-7.0 and a temperature range of 70-80° C. In addition, U.S. Pat. No. 5,395,765 discloses a xylanase derived from *Rhodothermus*, having activity over a pH range of 5-8 and thermostability at temperatures from 85-100° C. However, a xylanase with a more acidic pH range is desired for the utilization of hemicellulose biomass in fermentation.

The thermophilic cellulolytic bacterium *Acidothermus cellulolyticus* is described in Mohagheghi et al. (12), and the production of cellulase is described in Shiang et al. (19). However, neither reference describes a purified xylanase that may be useful at a low pH and high temperatures. U.S. Pat. No. 5,902,581 discloses a xylanase derived from *Acidothermus cellulolyticus* that is active at a pH range from 3.6-4.2 and that is thermostable at a range of 70-80° C. However, this *A. cellulolyticus* xylanase does not have optimal activity at temperatures above 80° C. or at a pH range from 4.5-6.0.

SUMMARY

Disclosed herein is a recombinant endo-beta-1,4-xylanase having an amino acid sequence with at least 80%, at least 85%, at least 87%, at least 89%, at least 90%, at least 91%, or at least 93% sequence identity to SEQ ID NO: 1. More preferably the amino acid sequence of the recombinant endo-beta-1,4-xylanase has at least 95%, at least 97%, or at least 99% sequence identity to SEQ ID NO: 1. In a particularly preferred embodiment, the amino acid sequence of the recombinant endo-beta-1,4-xylanase is SEQ ID NO: 1.

In certain embodiments, a region of the amino acid sequence of any of the recombinant endo-beta-1,4-xylanases described above conforms to consensus sequence: Pro-$Xaa_1$-Pro-$Xaa_2$-Pro (SEQ ID NO: 40). Preferably, $Xaa_1$ and $Xaa_2$ are each independently selected from no amino acid, any 1 amino acid, any 2 amino acids, or any 3 amino acids. In preferred embodiments, the amino acid sequence of any of the recombinant endo-beta-1,4-xylanases described above has a first Glu at a position corresponding to Glu-142 of SEQ ID NO: 1 and a second Glu at a position corresponding to Glu-259 of SEQ ID NO: 1. Preferably, the region of the amino acid sequence of any one of the recombinant endo-beta-1,4-xylanases described above is located between the first Glu and the second Glu. In certain embodiments, the first Glu is located within an amino acid region having a sequence of Asp-Val-Ala-Asn-Glu (SEQ ID NO: 25); and the second Glu is located within an amino acid region having a sequence of Thr-Glu-Ala-Asp (SEQ ID NO: 26).

In other preferred embodiments, $Xaa_1$ is one amino acid selected from His, Lys, or Arg; and $Xaa_2$ is one amino acid selected from Leu, Ala, Val, Ile, Pro, Phe, Met, or Trp. In particularly preferred embodiments, the region of the amino acid sequence of any of the recombinant endo-beta-1,4-xylanases described above is Pro-His-Pro-Leu-Pro (SEQ ID NO: 27).

In further embodiments, any of the recombinant endo-beta-1,4-xylanases described above can be active at pH values of about 3 to 9. In preferred embodiments, any of the endo-beta-1,4-xylanases described above have a pH optimum of about 4.5-6.0. In yet other embodiments, any of the recombinant endo-beta-1,4-xylanases described above have a molecular weight of about 40-48 kD. In further embodiments, any of the recombinant endo-beta-1,4-xylanases described above have activity at a temperature of at least 80° C. Preferably, any of the recombinant endo-beta-1,4-xylanases described above are active at least from 80-120° C. In particularly preferred embodiments, any of the recombinant endo-beta-1,4-xylanases described above have optimal activity at about 90° C.

In other embodiments, any of the recombinant endo-beta-1,4-xylanases described above retain at least 50% of initial activity, at 90° C., after incubation for at least 20 min, at least 30 min, at least 45 min, at least 60 min, at least 90 min, at least 2 hr, at least 5 hr, at least 8 hr, at least 12 hr, at least 24 hr, or at least 48 hr, at 90° C.

In yet other embodiments, any of the recombinant endo-beta-1,4-xylanases described above have a half-life of about 90 min at 90° C. in the presence of a xylan. In preferred embodiments, the xylan is birchwood xylan, beech wood xylan, or oat spelt xylan.

In certain embodiments, any of the recombinant endo-beta-1,4-xylanases described above further include a signal sequence peptide having amino acid sequence SEQ ID NO: 2.

In yet other embodiments, any of the recombinant endo-beta-1,4-xylanases described above has a substrate selected from lignocellulosic biomass, xylan-containing material, or xyloglucan-containing material.

The present disclosure also pertains to a recombinant cell comprising a nucleic acid molecule encoding any of the recombinant endo-beta-1,4-xylanases described above.

The present disclosure further pertains to a recombinant cell that expresses a nucleic acid molecule that has a nucleotide sequence with at least 80%, at least 85%, at least 87%, at least 89%, at least 90%, at least 91%, or at least 93% sequence identity to SEQ ID NO: 4, or its complementary sequence SEQ ID NO: 5. Preferably, the nucleic acid sequence of the nucleic acid molecule has at least 95%, at least 97%, or at least 99% sequence identity to SEQ ID NO: 4, or its complementary sequence SEQ ID NO: 5. In a particularly preferred embodiment, the nucleic acid sequence of the nucleic acid molecule is SEQ ID NO: 4, or its complementary sequence SEQ ID NO: 5.

The present disclosure also pertains to a method of hydrolyzing lignocellulose by contacting the lignocellulose with a recombinant endo-beta-1,4-xylanase having an amino acid sequence with at least 80%, at least 85%, at least 87%, at least 89%, at least 90%, at least 91%, at least 93%, at least 95%, at least 97%, or at least 99% sequence identity to SEQ ID NO: 1. Preferably, the lignocellulose is contacted with the recombinant endo-beta-1,4-xylanase at a temperature of at least 80° C., at least 85° C., at least 90° C., at least 95° C., or at least 100° C.; and a pH range from about 4.5-6.0. In a particularly preferred embodiment, the amino acid sequence of the recombinant endo-beta-1,4-xylanase is SEQ ID NO: 1.

The present disclosure further pertains to a method of hydrolyzing lignocellulose by contacting the lignocellulose with any of the recombinant endo-beta-1,4-xylanases described above. Preferably, the lignocellulose is contacted with the recombinant endo-beta-1,4-xylanase at a temperature of at least 80° C., at least 85° C., at least 90° C., at least 95° C., or at least 100° C.; and a pH range from about 4.5-6.0.

In other embodiments, the lignocellulose of any of the methods described above is from a source selected from birchwood, oat spelt, switchgrass, corn stover, miscanthus, energy cane, sorghum, eucalyptus, willow, bagasse, hybrid poplar, short-rotation woody crop, conifer softwood, crop residue, yard waste, or a combination thereof. In still other embodiments, the recombinant endo-beta-1,4-xylanase of any of the methods described above further includes a signal sequence peptide having amino acid sequence SEQ ID NO: 2.

DESCRIPTION OF DRAWING FIGURES

FIG. 1 is a table comparing various xylanases, all of which have temperature optima below 100° C. MW=molecular weight; T opt=optimal temperature range; and H opt=optimal ph range.

Figure 4:
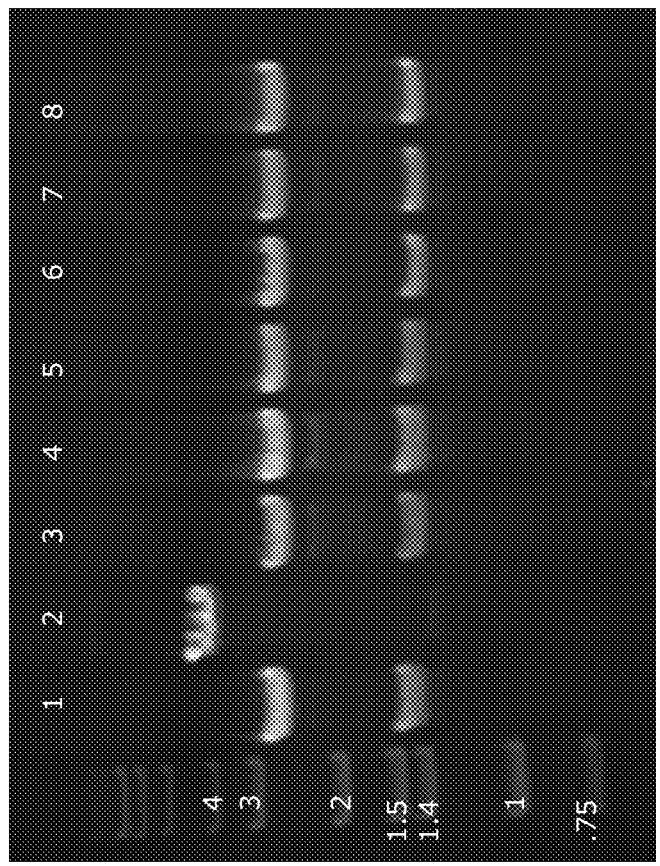

FIG. 4 is an image of an agarose gel depicting the results of purified plasmid clones containing the amplified xyl-1 gene Acel_0372. Leftmost lane, molecular weight marker (in kb); lanes 1 and 3-8 contain the correct constructs of pK19 (2.5 kb) containing the 1.4-kb PCR product after restriction digestion with SacI and XbaI. Lane 2 contains a pK19 construct that does not contain the 1.4-kb PCR product.

FIGS. 5 (A) and 5 (B) depict the nucleotide coding sequence of the PCR product amplified from *A. cellulolyticus* (SEQ ID NO: 4), the nucleotide complementary sequence of the PCR product amplified from *A. cellulolyticus* (SEQ ID NO: 5), and the amino acid sequence encoded by the PCR product amplified from *A. cellulolyticus* (SEQ ID NO: 3).

Figure 6:
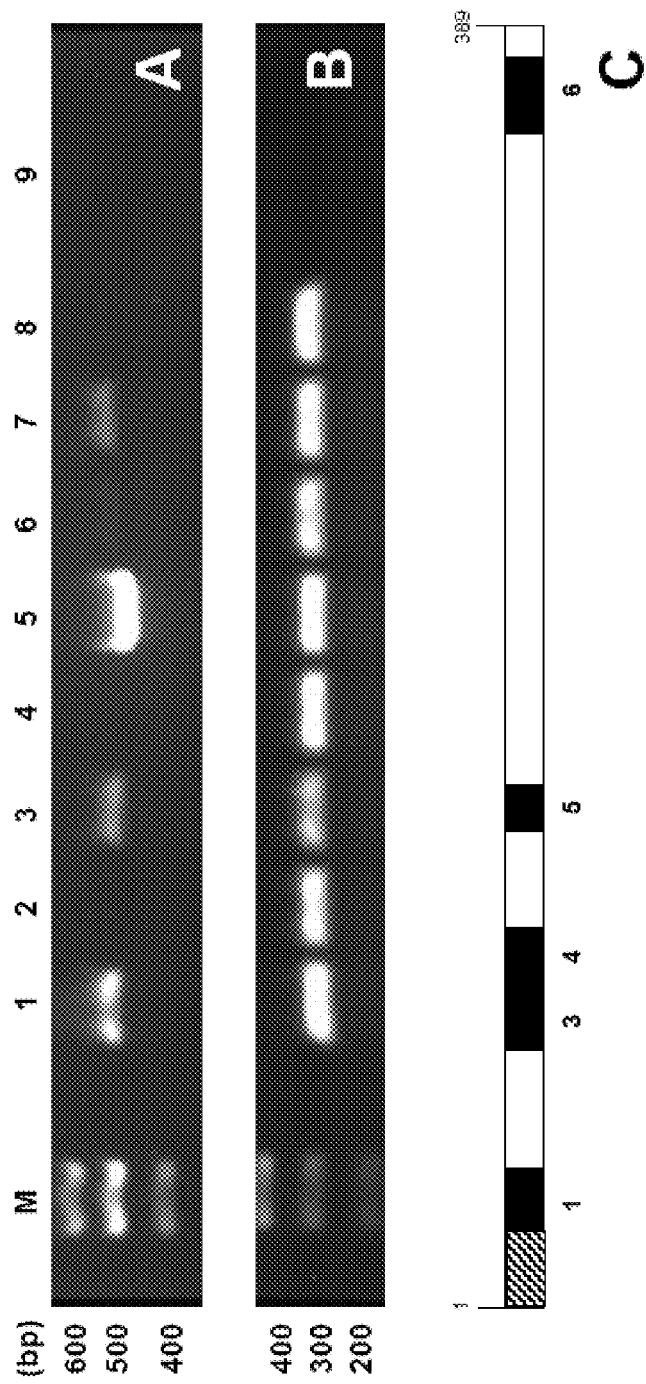

FIGS. 6 (A), 6 (B), and 6 (C) depict the expression of Xyl-1 in *A. cellulolyticus*. (A) RT-PCR analysis of the xyl-1 gene. (B) RT-PCR analysis of an internal control housekeeping gene, gyrB. M: molecular-weight DNA ladder, lanes 1-4: exponential growth phase samples, 5-8: stationary growth phase samples, and 9: no-RT negative control to confirm the absence of contaminating genomic DNA. Lanes 1 and 5: oat-spelt xylan-grown culture sample, 2 and 6: cellobiose-grown culture, 3 and 7: cellulose-grown culture, and 4 and 8: glucose-grown culture. (C) Representation of the peptide coverage of the Xyl-1 protein (389 aa) from tandem mass spectrometry of *A. cellulolyticus* culture supernatant. Hatched box indicates the N-terminal signal peptide, and black boxes indicate the positions of five non-overlapping peptides identified from the spectra. The peptides are as follows, 1: HGNPPYHPPADSLR (SEQ ID NO: 6), 2: WQVVEPTQGTYDWSGGDR (SEQ ID NO: 7), 3: LVQFAQEHGQLVR (SEQ ID NO: 8), 4: HIVDEVTHFK (SEQ ID NO: 9), and 5: PAYTALQQTLALAAGAPHR (SEQ ID NO: 10).

Figure 7:
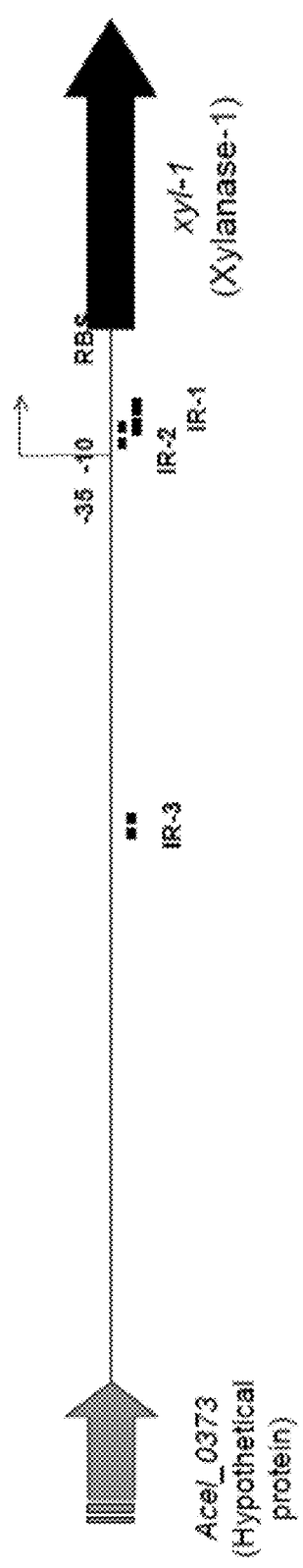

FIG. 7 depicts the full 451-bp untranslated intergenic region between the Acel_0373 and Acel_0372 (xyl-1) open reading frames. The sequence contains the xyl-1 promoter region. The putative –10 and –35 sequences are shown in bold and the putative Shine-Dalgarno ribosomal binding site (RBS) is also shown in bold. The Xyl-1 protein coding region is shown as a bold arrow at the end of the sequence. Three inverted repeats (IR-1, IR-2, and IR-3) are shown with bold letters and boxes. IR-1: GAAACTTTC (SEQ ID NO: 11), IR-2: TTTCCGAAA (SEQ ID NO: 12), and IR3: TCCGAAAATTTCGGA (SEQ ID NO: 13).

FIGS. 8 (A) and 8 (B) depict the purification of Xyl-1 by FPLC following heat treatment at 65° C. for 15 min. (A) Protein elution from the ion exchange column during the FPLC run as KCl concentration was increased. The black line is UV absorbance at 280 nm, the thin grey line indicates conductivity, and the thick grey line indicates the KCl gradient. (B) Activity profile (activity measured at 410 nm) at 52°

C., pH 5.2 was used to identify the fractions containing Xyl-1 that were then combined and concentrated.

FIGS. 9 (A) and 9 (B) depict the purification of Xyl-1 from *E. coli*. (A) Coomassie stained gel. (B) In-gel assay (carried out at 52° C., pH 5.2). Leftmost lane, molecular weight markers (in kD). CCE, crude cell extract from *E. coli* clone; ΔH, crude cell extract from *E. coli* clone after heat treatment (15 min at 65° C.); Main, concentrated active fractions from the ion exchange column; Side, concentrated side fractions. Asterisks indicate Xyl-1.

Figure 10:
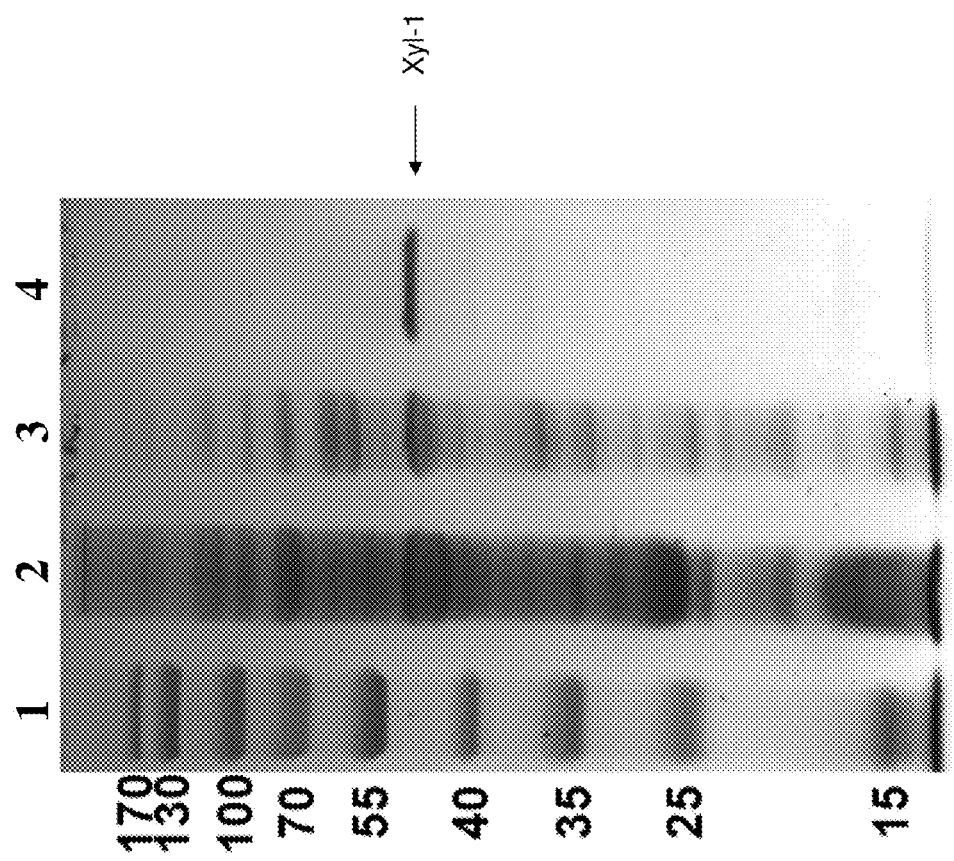

FIG. 10 depicts the purification of Xyl-1 by hydroxyapatite chromatography. SDS-PAGE (10% gel) analysis showing molecular weight markers (lane 1), crude cell extract from DH5α (pK19-xyl-1) (lane 2), heat treated (65° C. for 20 min followed by centrifugation) crude cell extract from DH5a (pK19-xyl-1) (lane 3), concentrated fractions from the hydroxyapatite column (lane 4).

Figure 11:
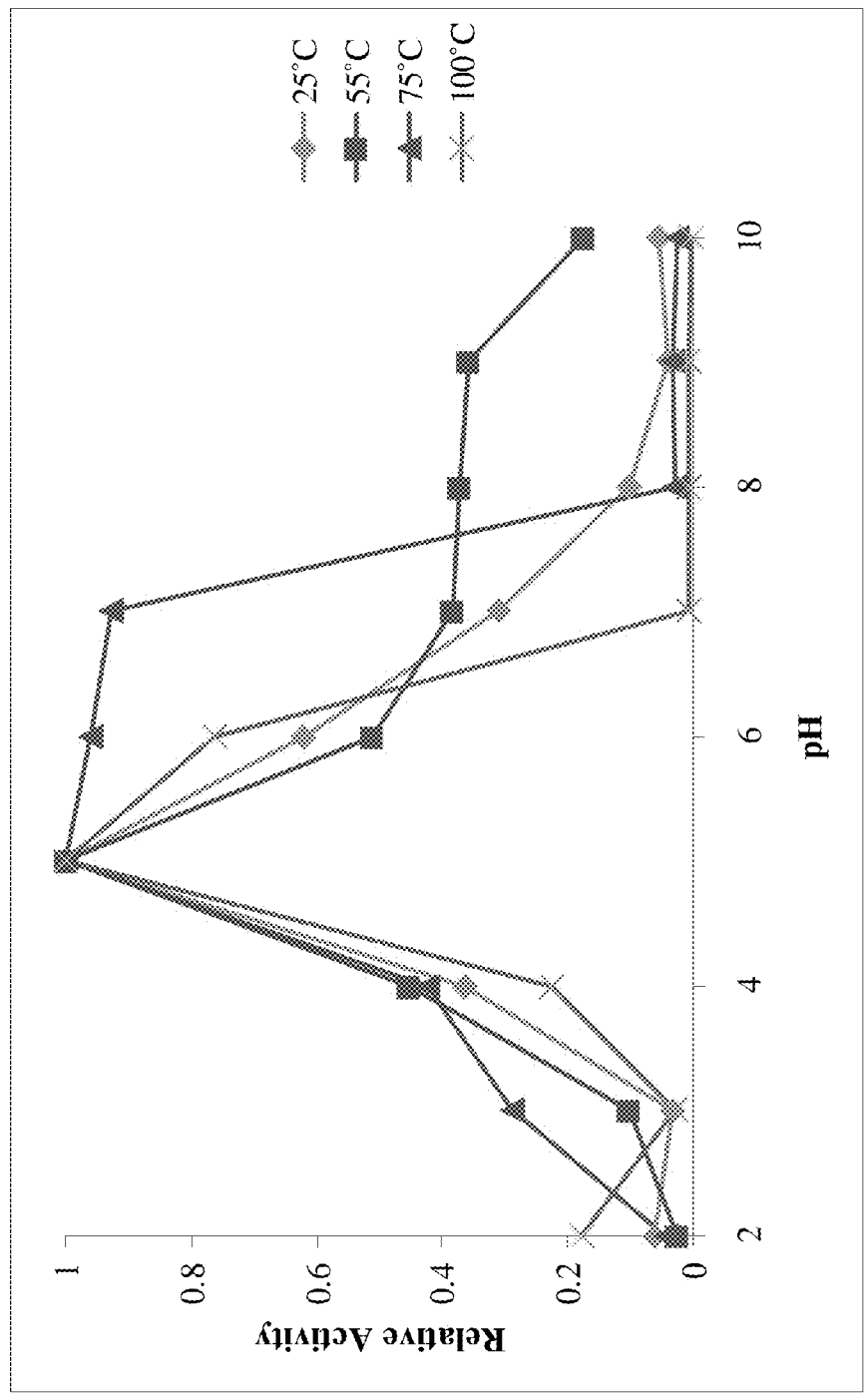

FIG. 11 depicts the relative activity of the partially purified Xyl-1 at various pH values and temperatures. Activity is relative to the highest activity at each pH.

Figure 12:
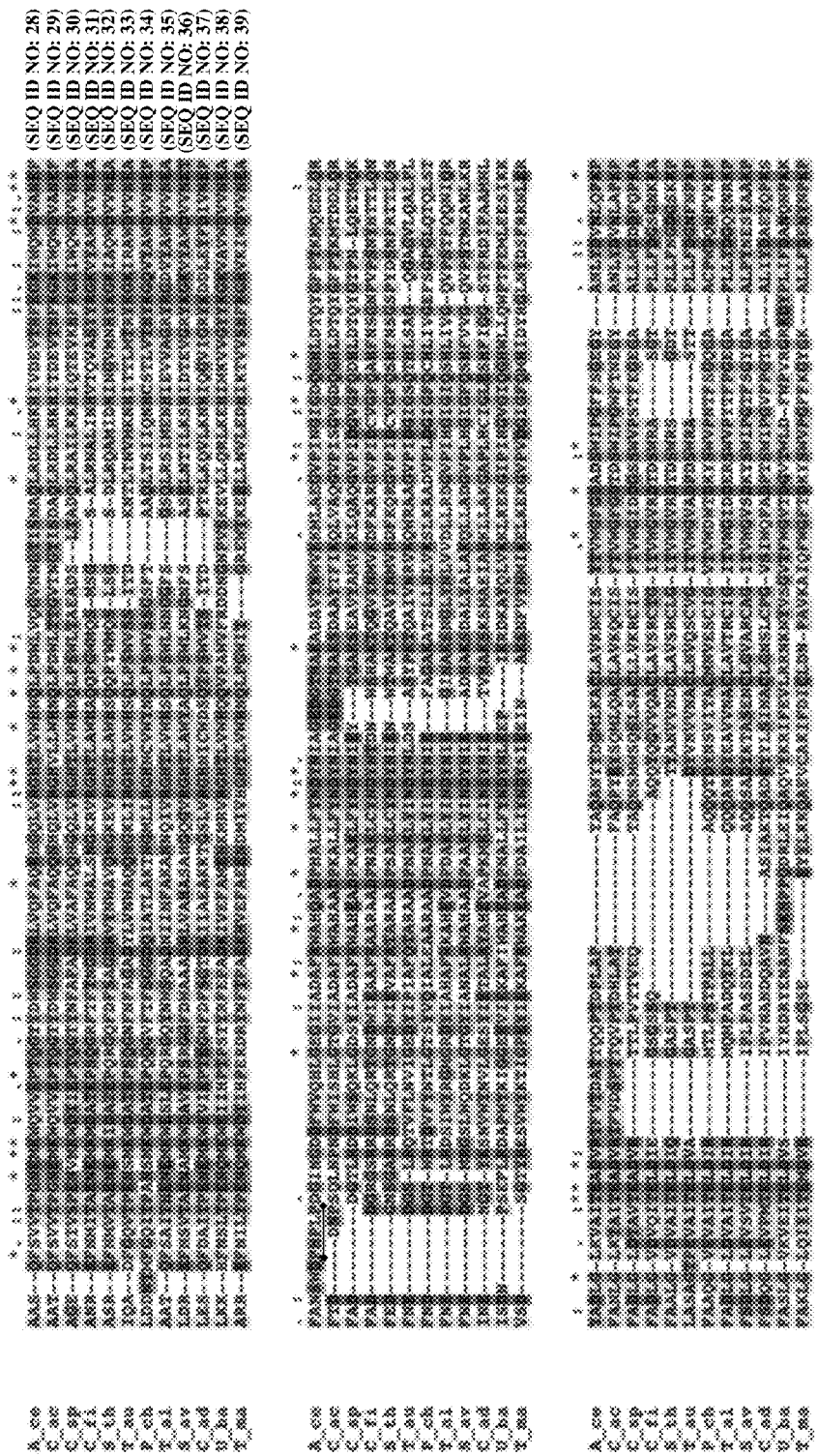

FIG. 12 depicts a multiple sequence alignment of Xyl-1 with other xylanases. A 295 amino acid fragment of Xyl-1 (residues 67-361) was aligned with eleven other homologs using Clustal X version 2.0 (26). Stars (*) indicate fully conserved sites, while colons (:) and periods (.) indicate sites with high and low degrees of conservation, respectively. The bar above the A_ce sequence indicates the unique Xyl-1 region of five amino acids containing three prolines. The abbreviations used and the accession numbers of the proteins are as follows: A_ce (*A. cellulolyticus* 11B Xyl-1, GI:117927581) (SEQ ID NO: 28); C_ac (*Catenulispora acidiphila* DSM 44928, GI:229247007) (SEQ ID NO: 29); C_sp (*Cellulosimicrobium* sp. HY-12, GI:162414427) (SEQ ID NO: 30); C_fi (*Cellulomonas fimi* ATCC 484, GI:73427793) (SEQ ID NO: 31); S_th (*Streptomyces thermoviolaceus*, GI:38524461) (SEQ ID NO: 32); T_au (*Thermoascus aurantiacus*, GI:13432255) (SEQ ID NO: 33); P_ch (*Phanerochaete chrysosporium*, GI:167599628) (SEQ ID NO: 34); T_al (*Thermobifida alba*, GI:1621277) (SEQ ID NO: 35); S_av (*Streptomyces avermitilis*, GI:29828638) (SEQ ID NO: 36); C_ad (*Cryptococcus adeliensis*, GI:2624008) (SEQ ID NO: 37); U_ba (Uncultured bacterium, GI:18476191) (SEQ ID NO: 38); and T_ma (*Thermotoga maritima*, GI:71041762) (SEQ ID NO: 39).

FIGS. 13 (A) and 13 (B) are images of an agarose gel that depicts an in-gel xylanase activity assay in *E. coli* crude cell extracts. Lanes ST, molecular weight standards (in kD); (A) lane 1, crude cell extracts from the vector control strain; lane 2, crude cell extracts from the Xyl-1 clone; (B) lane 3, crude cell extracts from the vector control after heat treatment (15 min at 65° C.); lane 4, crude cell extracts from the Xyl-1 clone strain after heat treatment. Assayed at 52° C., pH 5.2.

Figure 14:
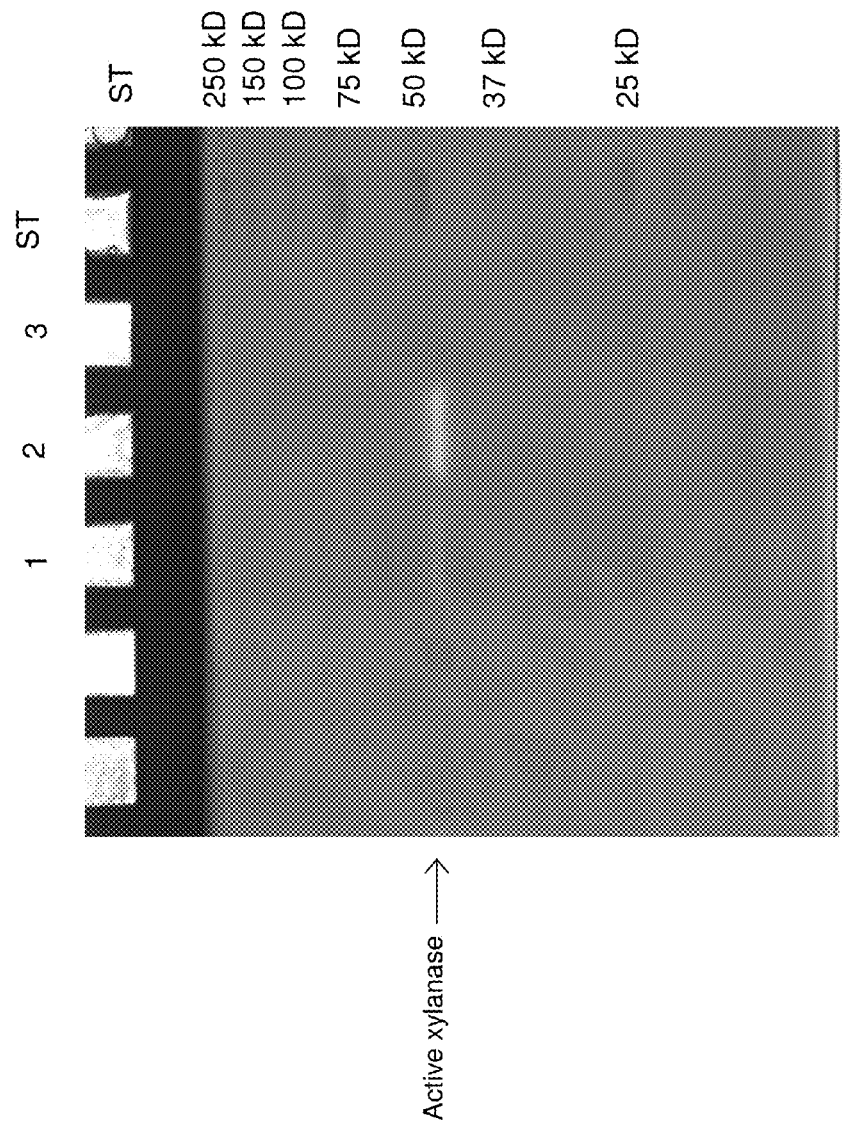

FIG. 14 is an image of a polyacrylamide gel that depicts xylanase activity in concentrated culture supernatants from the *E. coli* clone and *Acidothermus* (after growth on cellobiose) in the in-gel assay. Lanes ST, molecular weight standards (in kD); lane 1, *Acidothermus* culture supernatant; lane 2, Xyl-1 clone culture supernatant; lane 3, *E. coli* vector control culture supernatant. Assayed at 52° C., pH 5.2.

Figure 15:
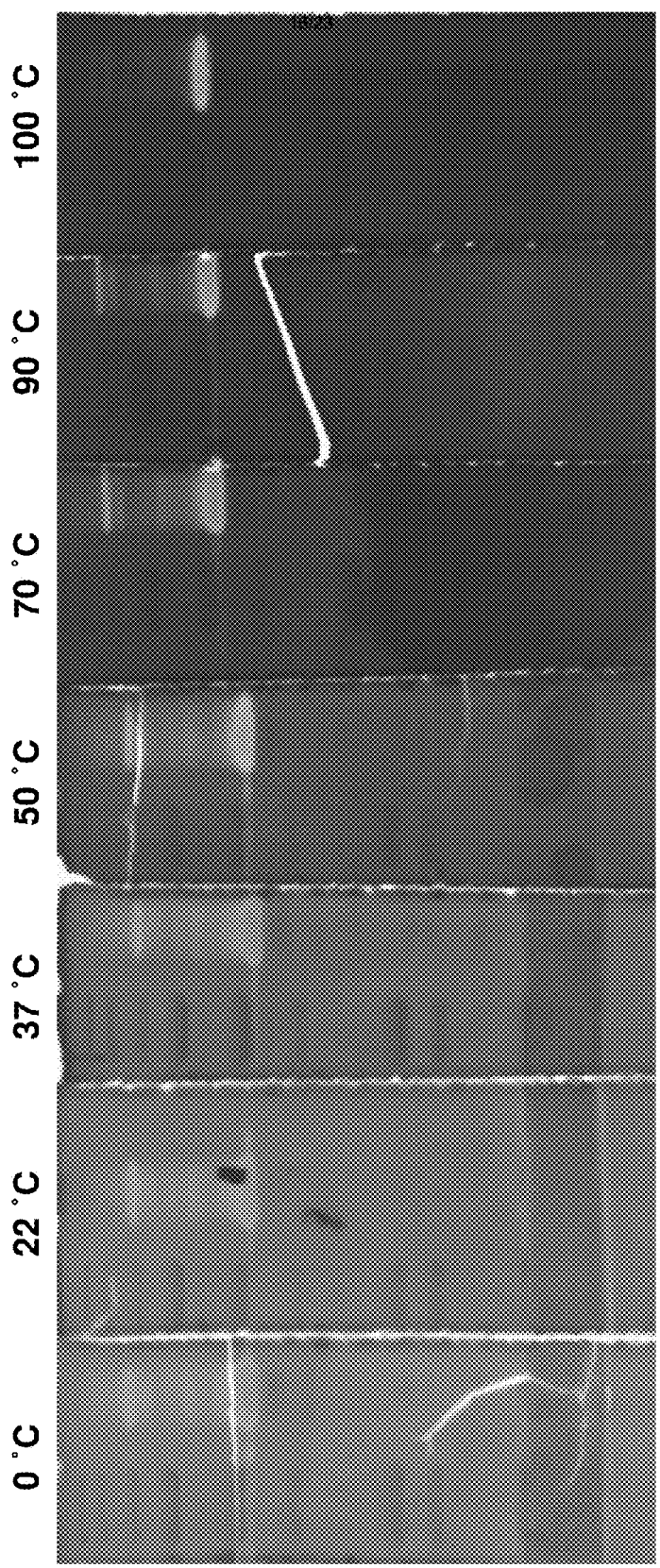

FIG. 15 is an image of a polyacrylamide gel that depicts the activity of recombinant Xyl-1 in *E. coli* crude cell extracts at temperatures ranging from 0-100° C. in the in-gel assay at pH 5.2.

Figure 16:
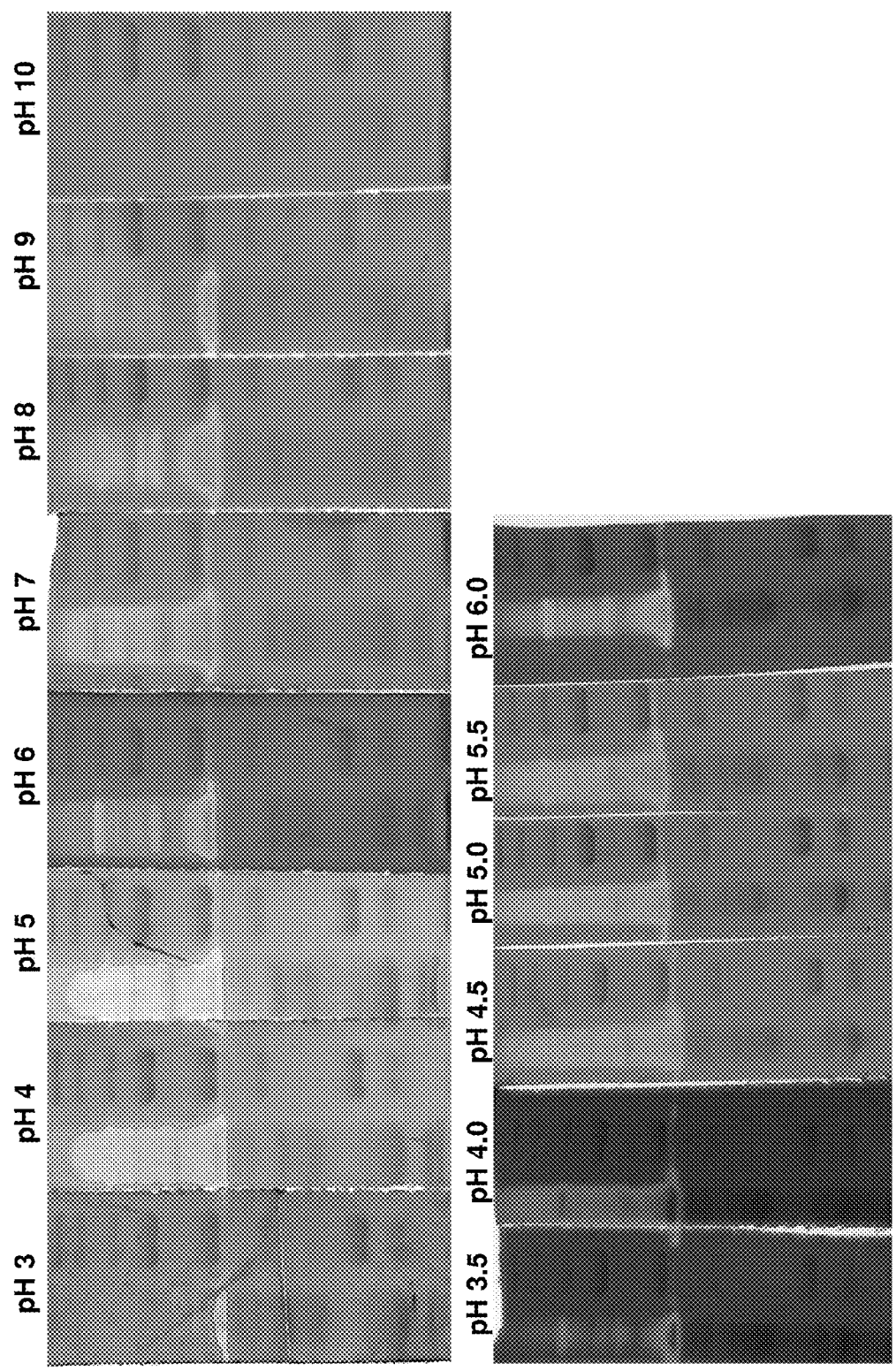

FIG. 16 is an image of a polyacrylamide gel that depicts activity of the recombinant Xyl-1 in *E. coli* crude cell extracts at pH values from 3-10 in the in-gel assay. Assays were carried out at 52° C.

Figure 17:
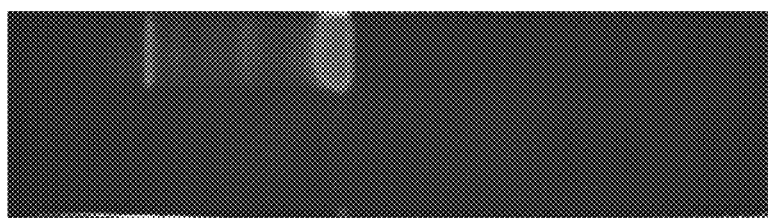

FIG. 17 is an image of a polyacrylamide gel that depicts activity of the recombinant Xyl-1 in *E. coli* crude cell extracts following heat treatment at 80° C. for 20 min. The assay was carried out at 52° C. and at pH 5.2.

Figure 18:
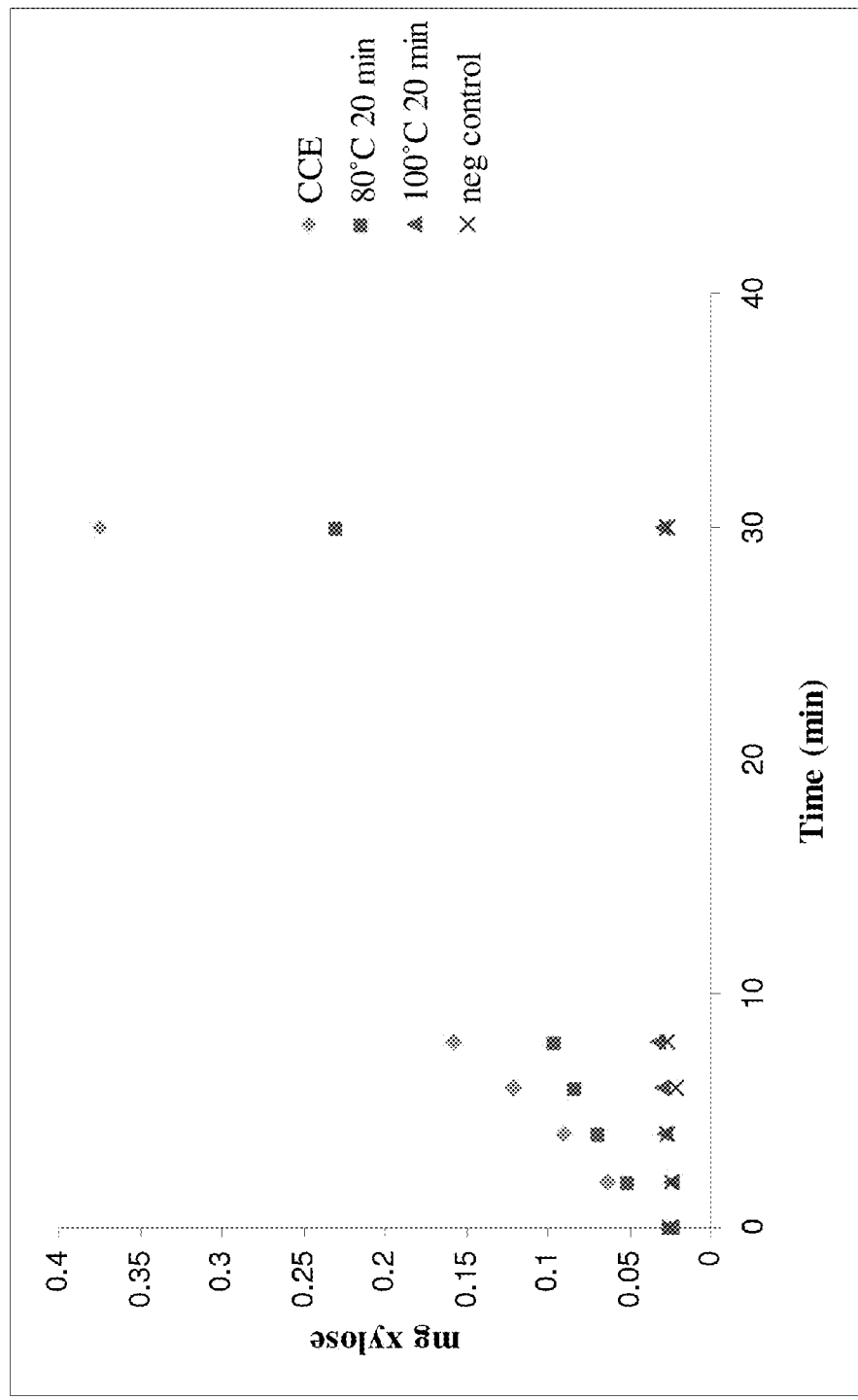

FIG. 18 depicts the activity of the recombinant Xyl-1 in *E. coli* crude cell extracts following heat treatment for 20 min. The assay was carried out at 52° C., pH 5.2.

Figure 19:
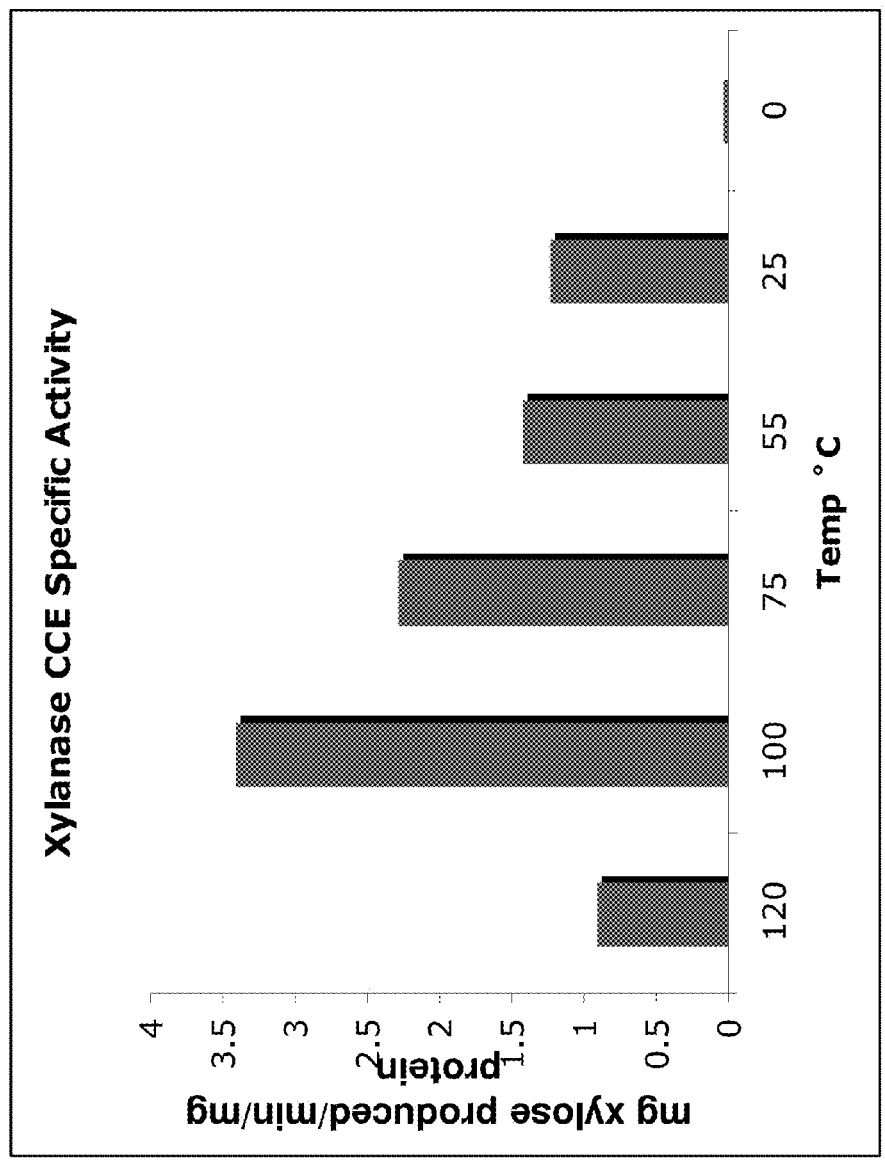

FIG. 19 depicts the specific activity of the recombinant Xyl-1 in *E. coli* crude cell extracts at temperatures from 0-120° C. at pH 5.2.

FIGS. 20 (A) and 20 (B) depict the temperature and pH profile of purified Xyl-1. (A) pH 3-6; (B) pH 7-10. Results are the averages of at least three independent experiments using the reducing sugars assay and oat spelt xylan as the substrate. Note that the activity ranges differ in A and B. Error bars indicate standard deviations.

FIGS. 21 (A) and 21 (B) depict the thermostability of recombinant Xyl-1. (A) Stabilization of the cloned Xyl-1 by xylan substrates. Purified Xyl-1 was diluted 1:20 with oat spelt xylan (light grey), birchwood xylan (grey) or phosphate buffer (white), and incubated at 90° C. for the times indicated. Rates were determined by the reducing sugars assay and are relative to the unheated Xyl-1 (black). Results are the averages of three independent experiments and error bars indicate standard deviations. (B) Activity retained by Xyl-1 in the presence of 3.8% oat spelt xylan. The half-life of Xyl-1 appears to be approximately 1.5 hr at 90° C.

FIGS. 22 (A) and 22 (B) depict the results of a TLC time course of Xyl-1 activity with oat spelt (A) and birchwood (B) xylans. The TLC was developed as described in Materials and Methods. Lanes 1 and 8, standard compounds: X1, xylose; X3, xylotriose; X4, xylotetraose. Lane 2, unreacted xylan; lanes 3-7, increasing time of incubation in the presence of purified Xyl-1. Lane 3, 10 min; lane 4, 20 min; lane 5, 40 min; lane 6, 60 min; lane 7, 240 min.

BRIEF DESCRIPTION OF THE SEQUENCE LISTING

SEQ ID NO: 1 shows the amino acid sequence of Xyl-1 without the N-terminal signal sequence.

SEQ ID NO: 2 shows the amino acid sequence of the N-terminal Xyl-1 signal sequence.

SEQ ID NO: 3 shows the amino acid sequence encoded by the PCR product amplified from *A. cellulolyticus*.

SEQ ID NO: 4 shows the nucleotide coding sequence of the PCR product amplified from *A. cellulolyticus*.

SEQ ID NO: 5 shows the nucleotide complementary sequence of the PCR product amplified from *A. cellulolyticus*.

SEQ ID NO: 6 shows the amino acid sequence of the first of five non-overlapping Xyl-1 peptides identified by tandem mass spectrometry of *A. cellulolyticus* culture supernatant.

SEQ ID NO: 7 shows the amino acid sequence of the second of five non-overlapping Xyl-1 peptides identified by tandem mass spectrometry of *A. cellulolyticus* culture supernatant.

SEQ ID NO: 8 shows the amino acid sequence of the third of five non-overlapping Xyl-1 peptides identified by tandem mass spectrometry of *A. cellulolyticus* culture supernatant.

SEQ ID NO: 9 shows the amino acid sequence of the fourth of five non-overlapping Xyl-1 peptides identified by tandem mass spectrometry of *A. cellulolyticus* culture supernatant.

SEQ ID NO: 10 shows the amino acid sequence of the fifth of five non-overlapping Xyl-1 peptides identified by tandem mass spectrometry of *A. cellulolyticus* culture supernatant.

SEQ ID NO: 11 shows the nucleotide sequence of the first of three inverted repeats (IR-1) located in the xyl-1 promoter region.

SEQ ID NO: 12 shows the nucleotide sequence of the second of three inverted repeats (IR-2) located in the xyl-1 promoter region.

SEQ ID NO: 13 shows the nucleotide sequence of the third of three inverted repeats (IR-3) located in the xyl-1 promoter region.

SEQ ID NO: 14 shows the nucleotide sequence of the forward primer used to PCR amplify Acel_0372.

SEQ ID NO: 15 shows the nucleotide sequence of the reverse primer used to PCR amplify Acel_0372.

SEQ ID NO: 16 shows the nucleotide sequence of a forward primer specific to the xyl-1 gene.

SEQ ID NO: 17 shows the nucleotide sequence of a reverse primer specific to the xyl-1 gene.

SEQ ID NO: 18 shows the nucleotide sequence of a forward gyrB gene-specific primer.

SEQ ID NO: 19 shows the nucleotide sequence of a reverse gyrB gene-specific primer.

SEQ ID NO: 20 shows the nucleotide sequence of the putative xyl-1 ribosomal binding site (RBS).

SEQ ID NO: 21 shows the nucleotide sequence of the conserved sequence found at the 3' end of the *A. cellulolyticus* 16S ribosomal rRNA that is complimentary to the RBS sequence.

SEQ ID NO: 22 shows the amino acid sequence of the N-terminal sequence of the recombinant Xyl-1.

SEQ ID NO: 23 shows the conserved amino acid sequence of the first active site glutamate region of GH10 family xylanases.

SEQ ID NO: 24 shows the conserved amino acid sequence of the second active site glutamate region of GH10 family xylanases.

SEQ ID NO: 25 shows the amino acid sequence of the first active site glutamate region of Xyl-1.

SEQ ID NO: 26 shows the amino acid sequence of the second active site glutamate region of Xyl-1.

SEQ ID NO: 27 shows the amino acid sequence of the region containing three prolines close to the first active site glutamate of Xyl-1.

SEQ ID NO: 28 shows the amino acid sequence of a 295 amino acid fragment of Xyl-1 (i.e., residues 67-361)

SEQ ID NO: 29 shows the amino acid sequence of *Catenulispora acidiphila* DSM 44928 (GI:229247007) xylanase.

SEQ ID NO: 30 shows the amino acid sequence of *Cellulosimicrobium* sp. HY-12 (GI:162414427) xylanase.

SEQ ID NO: 31 shows the amino acid sequence of *Cellulomonas fimi* ATCC 484 (GI:73427793) xylanase.

SEQ ID NO: 32 shows the amino acid sequence of *Streptomyces thermoviolaceus* (GI:38524461) xylanase.

SEQ ID NO: 33 shows the amino acid sequence of *Thermoascus aurantiacus* (GI:13432255) xylanase.

SEQ ID NO: 34 shows the amino acid sequence of *Phanerochaete chrysosporium* (GI:167599628) xylanase.

SEQ ID NO: 35 shows the amino acid sequence of *Thermobifida alba* (GI:1621277) xylanase.

SEQ ID NO: 36 shows the amino acid sequence of *Streptomyces avermitilis* (GI:29828638) xylanase.

SEQ ID NO: 37 shows the amino acid sequence of *Cryptococcus adeliensis* (GI:2624008) xylanase.

SEQ ID NO: 38 shows the amino acid sequence of an uncultured bacterium (GI:18476191) xylanase.

SEQ ID NO: 39 shows the amino acid sequence of *Thermotoga maritima* (GI:71041762) xylanase.

SEQ ID NO: 40 shows the amino acid sequence of a Xyl-1 proline rich consensus sequence.

DETAILED DESCRIPTION

Definitions

As used herein, the term "thermostable" refers to a threshold level of xylanase activity after an incubation period of 15 min at a temperature of 65° C.

As used herein, the terms "active" and "activity" refer to an endo-beta-1,4-xylanase giving a positive result using the in-gel xylanase assay or the reducing sugar assay described below.

As used herein, the term "percent activity" refers to the amount of endo-beta-1,4-xylanase activity measured at given experimental conditions compared to base-line xylanase activity. The measured xylanase activity at experimental conditions is divided by the base-line xylanase activity and multiplied by 100 to obtained percent activity. As used herein, "base-line xylanase activity" and "baseline control" refer to the amount of xylanase activity produced by an endo-beta-1,4-xylanase when assayed at 55° C. and pH 5.2 for 10 min.

As used herein, the term "half-life" refers to the length of time necessary for an endo-beta-1,4-xylanase activity to drop by 50% (compared to base-line control) at a given temperature.

As used herein, the term "optimal activity" refers to peak xylanase activity in a given temperature range or range of pH values.

As used herein, the term percent "identical," "percent identity," and "percent sequence identity" are defined as amount of identity between a reference nucleic acid or amino acid sequence and at least one other nucleic acid or amino acid sequence. Percent sequence identity can be determined by comparing two optimally aligned sequences, wherein the portion of the sequence being compared may comprise additions or deletions (i.e., gaps) as compared to the reference sequence (e.g., a nucleic acid or amino acid sequence of the disclosure), which does not comprise additions or deletions, for optimal alignment of the two sequences. The percentage is calculated by determining the number of positions at which the identical nucleic acid or amino acid residue occurs in both sequences to yield the number of matched positions, dividing the number of matched positions by the total number of positions being compared and multiplying the result by 100 to yield the percentage of sequence identity. Two sequences have percent identity if two sequences have a specified percentage of nucleic acids or amino acid residues that are the same (i.e., 75% identical over a specified region, or, when not specified, over the entire sequence), when compared and aligned for maximum correspondence or designated region as measured using one of the following sequence comparison algorithms or by manual alignment and visual inspection.

One example of an algorithm that is suitable for determining percent sequence identity is the BLAST algorithm, which is described in Altschul et al. (1977) Nuc. Acids Res. 25:3389-3402. Software for performing BLAST analyses is publicly available through the National Center for Biotechnology Information. The BLASTN program (used for nucleic acid sequences) uses as defaults a wordlength (W) of 11, an expectation (E) or 10, M=5, N=−4 and a comparison of both strands. For amino acid sequences, the BLASTP program is used with default settings of a wordlength of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=−4, and a comparison of both strands.

*Acidothermus Cellulolyticus* Xyl-1 Xylanase

The following description sets forth numerous exemplary configurations, parameters, and the like. It should be recognized, however, that such description is not intended as a limitation on the scope of the present invention, but is instead provided as a description of exemplary embodiments.

*Acidothermus cellulolyticus* 11B (ATCC 43068) is a thermophilic bacterium that was originally isolated from an acidic hot spring in Yellowstone National Park. A number of thermostable endoglucanases are produced by this organism, which are useful for degrading cellulose in the production of ethanol or other hydrocarbons for biofuel. The genome of *Acidothermus cellulolyticus* 11B (henceforth referred to as *A. cellulolyticus*) has been sequenced to completion (Refseq NC_008578) and the sequence has been annotated. The sequence and sequence annotation have provided information on the regulation and production of potentially useful enzymes (published as accession number NC_008578). Among these potentially useful enzymes, the *A. cellulolyticus* sequence annotation predicted a single putative endo-beta-1,4-xylanase, which is encoded by Acel_0372 (from the *A. cellulolyticus* genome annotation). It is believed that there are no reports of this endo-beta-1,4-xylanase having been previously cloned, and the predicted molecular weight does not match the previously disclosed *A. cellulolyticus* xylanase (U.S. Pat. No. 5,902,581). Therefore, this predicted endo-beta-1,4-xylanase was cloned from *A. cellulolyticus*, and expressed as a recombinant protein.

The expressed protein encoded by Acel_0372 was identified as a glycosyl hydrolase family 10 (GH10) endo-beta-1,4-xylanase enzyme. This *A. cellulolyticus* GH10 family xylanase was named Xyl-1. Characterization of Xyl-1 revealed that it is a thermophilic xylanase that has a temperature optimum of 90° C. and a pH optimal range of about 4.5-6.0. Xyl-1 is also characterized by retaining xylanase activity at a temperature range of 25-120° C., and a pH range of 3-9. Xyl-1 also has a molecular weight of about 40-48 kD. Furthermore, Xyl-1 is distinct from the *A. cellulolyticus* xylanase disclosed in U.S. Pat. No. 5,902,581 in that it has an optimal temperature range that is higher than the 70-80° C. range of the xylanase disclosed in U.S. Pat. No. 5,902,581, has a pH range that is less acidic than the pH range of 3.6-4.2 of the xylanase disclosed in U.S. Pat. No. 5,902,581, and is smaller in size than the 50-55 kD xylanase disclosed in U.S. Pat. No. 5,902,581.

It is surprising and unexpected that *A. cellulolyticus* produces a second xylanase (i.e., Xyl-1), different in optimal temperature and pH range from the previously identified xylanase (U.S. Pat. No. 5,902,581).

As stated above, Xyl-1 is useful in degrading (e.g., hydrolyzing) xylan-containing material, xyloglucan-containing material, and lignocellulosic biomass in the production of ethanol or other hydrocarbons for biofuel. For example, Xyl-1 can be used to hydrolyze lignocellulosic biomass from birchwood, oat spelt, switchgrass, corn stover, miscanthus, energy cane, sorghum, eucalyptus, willow, bagasse, hybrid poplar and other short-rotation woody crops, various species of conifer softwood, various crop residues, or yard waste in order to improve the availability of fermentable sugars in these substrates. In industrial applications, the hydrolysis step is preferably performed at temperatures from 50° C.-100° C. and at acidic pH values. The stability of Xyl-1 over a wide range of temperatures and pH values provides versatility in industrial processes. Additionally, Xyl-1 provides long-lived and persistent xylanase activity under fluctuating conditions, which can occur in large-scale bioconversion systems. These conditions may further allow for the advantageous coupling of lignocellulose hydrolysis to lignocellulose fermentation.

Xyl-1 can also be used to bleach lignocellulosic pulp as a step in the process of making paper, to improve animal feed by making feed more digestible, or Xyl-1 can be used as a component in a detergent composition.

The xylanases of this disclosure, methods of their manufacture, and methods of their use may be better understood with respect to the following non-limiting examples.

EXAMPLES

Example 1

Cloning of the Xyl-1

Figure 2:
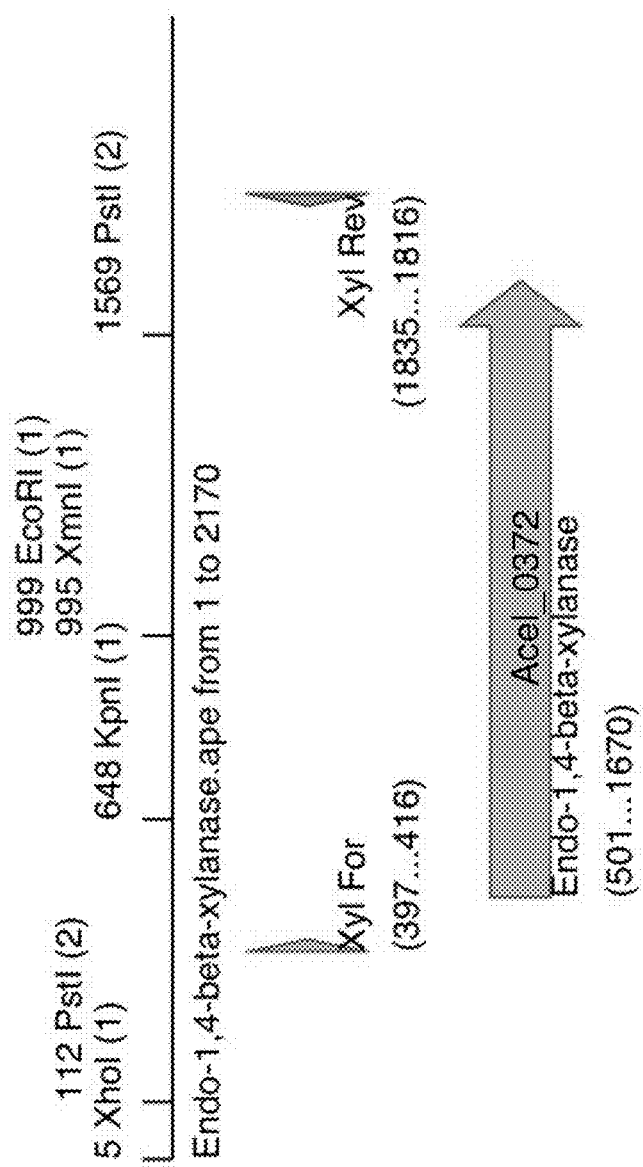
FIG. 2 depicts a diagram of the *A. cellulolyticus* xyl-1 gene Acel_0372.
Figure 3:
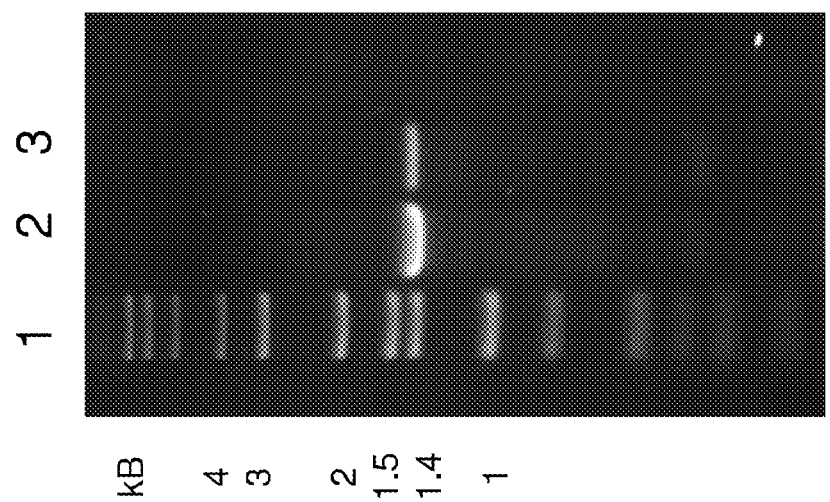
FIG. 3 is an image of an agarose gel, depicting the results of PCR amplification of the xyl-1 gene Acel_0372. Lane 1, molecular weight marker; lanes 2 and 3, PCR products from amplifications containing two different concentrations of *A. cellulolyticus* genomic DNA as the template.

According to the *A. cellulolyticus* 11B genome annotation, Acel_0372 encodes a predicted secreted xylanase (Xyl-1). In order to clone Acel_0372, *A. cellulolyticus* 11B (ATCC 43068) genomic DNA was purified as previously described (15), and oligonucleotide primers were designed in order to PCR amplify the complete Acel_0372, the predicted 1.4-kb Xyl-1 gene from *A. cellulolyticus* (FIG. 2). The primer pair used was Xyl For (5'-GTG GTG <u>GAGCTC</u> GCA ATT CGT TCA CGT TGA GG-3') (SEQ ID NO: 14) and Xyl Rev (5'-GTG GTG <u>TCTAGA</u> ACC ATC GAG TGG GAG TGA CG-3') (SEQ ID NO: 15). The underlined sequences indicate the added restriction sites for cloning, SacI and XbaI, respectively. PCR was performed using the following program using Pfu: an initial denaturation at 95° C. for 3 min, followed by 25 cycles of 95° C. for 1 min, 55° C. for 1 min, 70° C. for 1 min, and then a final extension at 70° C. for 5 min. The PCR yielded a 1.4-kb product, which is the xyl-1 gene (FIG. 3). The resulting 1.4-kb PCR product was purified from an agarose gel with a QIAquick Gel Extraction kit (Qiagen, Valencia, Calif.), digested with SacI and XbaI and ligated to SacI-XbaI-digested pK19 (16). *E. coli* DH5α cells were transformed with plasmid DNA by standard procedures (18). Clones were confirmed by restriction digestion with SacI and XbaI (FIG. 4).

DNA sequence analysis was performed on the positive pK19 clones containing the xyl-1 gene (FIG. 5). Fluorescent automated DNA sequencing was carried out at the University of California, Davis sequencing facility with an Applied Biosystems 3730 automated sequencer. Nucleotide and amino acid sequence analyses were performed using the Vector NTI software suite (Invitrogen, Carlsbad, Calif.). The complete sequence of the xyl-1 gene was identical to the sequence reported for Acel_0372.

Example 2

Xyl-1 expression in *A. cellulolyticus*

Materials and Methods

*A. cellulolyticus* cultures were grown in supplemented mineral medium as described previously (12). Oat spelt xylan, cellulose, cellobiose, or glucose were provided individually as carbon sources at 0.5%. Cells were grown to mid exponential phase or stationary phase and cells were harvested by centrifugation at 10,000×g for 15 min at 4° C. The cell pellet was frozen in liquid nitrogen and cells were disrupted by grinding with a mortar and pestle prechilled in liquid nitrogen, in the presence of sterilized sand. RNA was extracted using the RNeasy Plant Mini Kit (Qiagen), with several rounds of DNase digestion with RNase-free DNase (Qiagen), and cleaned with the RNeasy Plant Mini Kit. For the cultures grown on oat spelt xylan or cellulose, high molecular weight polyethylene glycol (at 1% w/v final concentration) was added to the cell lysate to reduce the amount of contaminating genomic DNA. It was found that several rounds of DNase digestion were required to completely eliminate DNA contamination. The quality of the RNA was analyzed using an Agilent Bioanalyzer 2100 (Agilent Technologies) and quantified using a Nanodrop spectrophotometer (Thermo Scientific).

Primers specific to the xyl-1 gene (primers: 5'-CAAAG-GAAAGATCTGGCAATG-3' (SEQ ID NO: 16) and 5'-TGAGCATCCCGTCGTAGTAGT-3' (SEQ ID NO: 17)) were used to amplify a 485-bp product from 100 ng total RNA template using reverse transcriptase polymerase chain reaction (RT-PCR). The Qiagen OneStep RT-PCR kit was used. The amplified products were analyzed on agarose gels and photographed using the Red gel imaging system (Alpha Innotech). The gyrB gene-specific primers 5'-GACCCGAC-CGAGGTTTATTAC-3' (SEQ ID NO: 18) and 5'-GC-CGAACTTGTTCACCAAATA-3' (SEQ ID NO: 19) were used to amplify a 270-bp product that was used to normalize for the RNA loaded as well as for semi-quantification of the xyl-1 expression. For biological replications of the experiment, RT-PCR was repeated using a second batch of RNA that was extracted independently under all growth conditions. Identical results were obtained in duplicate experiments, and data from one of the replicates are presented.

For proteomics analysis, *A. cellulolyticus* was grown on oat spelt xylan to stationary phase and culture supernatant was harvested by centrifugation. The culture supernatant was concentrated by a factor of 50 using an Amicon stirred ultrafiltration cell carrying a polyethersulfone membrane with 5-kDa molecular weight cutoff (Millipore). For identification of proteins in the concentrated culture supernatant, the sample was subjected to liquid chromatography followed by tandem mass spectrometry (LC/MS/MS) at the University of California Davis Proteomics Core facility.

Results

The transcriptional expression of the *A. cellulolyticus* xyl-1 gene was studied during exponential as well as stationary phases of growth on oat spelt xylan, cellulose, cellobiose, and glucose. The RT-PCR analysis revealed that xyl-1 was expressed in xylan- and cellulose-grown cultures (FIG. 6A). The gene was also expressed at low levels in cellobiose-grown cultures during stationary phase. No expression was detectable in glucose-grown cultures at any time or in cellobiose-grown cultures during exponential phase. In xylan- and cellulose-grown cultures, xyl-1 expression appeared to be essentially the same during the exponential and stationary phases of growth. The gyrB gene was used as an internal control to normalize the expression levels of the xyl-1 gene (FIG. 6B).

Tandem mass spectrometry verified the presence of Xyl-1 in the culture supernatant (FIG. 6C) and indicated that the N-terminal 25 aa signal peptide, which targets proteins for secretion, was cleaved from the mature protein.

Example 3

Sequence Analysis of Xyl-1 Gene Promoter

The xyl-1 gene was determined to be on the negative strand and is separated by 147 bp from the divergently oriented upstream gene, and 451 bp from the downstream gene on the negative strand. The functions of both of these flanking genes appear to be unrelated to xylanases. Thus, xyl-1 does not appear to be part of a gene cluster or operon. Analysis of the 451-bp upstream promoter region revealed a putative Shine-Dalgarno ribosomal binding site (RBS) six nucleotides upstream of the translational start. The RBS sequence (5' TGGAGG 3') (SEQ ID NO: 20) is complementary to the conserved CCTCCT (SEQ ID NO: 21) sequence found at the 3' end of the *A. cellulolyticus* 16S ribosomal rRNA, with only a one-base mismatch (FIG. 7). Putative −35 and −10 sequences were also identified (FIG. 7) that match well with the consensus promoter motifs proposed in the closely-related actinomycete, *Streptomyces* (20), and are likely to be the $\sigma^{70}$ promoter sequences of the *A. cellulolyticus* xyl-1 gene.

Several small inverted repeats were found in the promoter region of xyl-1 using the palindrome software in EMBOSS (17). Among these, three inverted repeats (FIG. 7) were found to be conserved based on comparison to the promoter regions of GH10 family xylanases in *Streptomyces* sp. (6). The sequences of the three inverted repeats, IR-1, IR-2, and IR-3, in the xyl-1 promoter match well with the consensus sequences of Box 1, Box 2, and Box 3, respectively, described for some GH10 family xylanase genes in *Streptomyces* spp. (6). However, the length and positioning of these putative regulatory elements in the two organisms are very different. In the xyl-1 promoter, the distal IR-1 sequence forms a short palindrome (5' GAAA-C-TTTC 3') (SEQ ID NO: 11) and the downstream IR-3 palindrome extends three nucleotides longer (5' TCCGAAA-A-TTTCGGA 3') (SEQ ID NO: 13), whereas the Box 3 palindrome is one-nucleotide longer than the Box 1 in *Streptomyces*. The *A. cellulolyticus* IR-2 sequence (5' TTTC-C-GAAA 3') (SEQ ID NO: 12) is almost identical to the *Streptomyces* Box 2 sequence. However, unlike in *Streptomyces*, where Box 1 and Box 2 are separated by about 10 bp, the xyl-1 IR-2 element overlaps with IR-1 (FIG. 7). Furthermore, in *A. cellulolyticus*, the IR-1 and IR-2 regions are located downstream of the putative −35 and −10 elements and closer to the translational start site, while both of the corresponding boxes are upstream of the promoter, and farther away from the first codon in *Streptomyces*.

Example 4

Xyl-1 Protein Purification

Materials and Methods

*E. coli* DH5α cells containing the cloned xyl-1 gene were grown in a minimal salts medium containing 10 mM glucose, 1 mM thiamine and 100 µg/ml kanamycin at 30° C. for 48 hr. Cells were harvested by centrifugation (14,000×g at 4° C. for 15 min), washed once with 10 mM phosphate buffer (pH 5.2), resuspended in the same buffer and stored frozen at −20° C. Frozen cell suspensions were removed from the freezer and allowed to thaw on ice. The thawed cell suspension was then passed once through a French pressure cell maintaining the internal cell pressure a constant 18,000 psi. Cell debris and membranes were removed by centrifugation at 48,000×g for 90 min at 6° C. The resulting crude cell extract was heat-treated by incubation at 65° C. for 20 min. Insoluble material was removed by centrifugation at 14,000×g at 4° C. for 15 min. Purification procedures were performed at 4° C. using an automated FPLC system (Bio-Rad Laboratories, Hercules, Calif.). Cell extracts were applied to a column containing approximately 100 ml (bed volume) of Unosphere Q (Bio-Rad Laboratories) that had been pre-equilibrated with 10 mM phosphate buffer (pH 5.2). Unbound proteins were eluted from the column with 100 ml of the same buffer at a rate of 1.0 ml/min. Bound proteins were eluted with a linear gradient from 0 to 1.0 M KCl in phosphate buffer at the same flow rate and 5 ml fractions were collected.

Results

Extracts of the *E. coli* clone were subjected to heat treatment at 65° C. for 15 min prior to loading the extract onto an ion exchange column. Xyl-1 protein eluted as one major peak with activity (FIG. 8). This heat treatment eliminated many of the *E. coli* proteins and resulted in a significant purification of Xyl-1 (FIG. 9). The concentrated protein was >90% pure, as determined by SDS-PAGE analysis (FIGS. 9 and 10). Approximately 2 mg of purified Xyl-1 was obtained from 4 L of *E. coli* culture. The recombinant Xyl-1 had a molecular weight of approximately 40-48 kD on SDS gels (FIGS. 9 and 10), which is consistent with the predicted molecular weight based on the deduced amino acid sequence of the processed protein (40.3 kD).

A temperature vs. pH profile with the partially purified Xyl-1 demonstrated that the enzyme has a broad temperature range with optimal activity at approximately 90° C. and a broad pH range with an optimum between pH 4.5 and 6.0 (FIG. 11).

Example 5

Xyl-1 N-Terminal Amino Acid Sequence Analysis

Samples of recombinant Xyl-1 purified from *E. coli*, as described in Example 4, were used to determine whether Xyl-1, an extracellular enzyme, was properly processed in *E. coli*. The N-terminal amino acid sequence of the purified Xyl-1 was determined by Edman degradation on an automated sequencer (Applied Biosystems, Foster City, Calif.) at the University of California Davis Molecular Structure Facility after SDS-PAGE and electroblotting of the purified proteins onto a polyvinylidene difluoride membrane (ProBlott; Applied Biosystems).

The N-terminal sequence of the recombinant Xyl-1 expressed in *E. coli* was found to be HGNPPYHPPAD (SEQ ID NO: 22). The first amino acid of this sequence mapped to position 26 in the full-length protein sequence, indicating that the predicted signal sequence of Xyl-1 was properly cleaved in the heterologous host, *E. coli* (FIG. 5). This indicates that the *E. coli* cells processed Xyl-1 by cleaving the signal sequence, which is the secretion signal sequence. As is the case with the native *A. cellulolyticus* 11B xylanase, Xyl-1 expressed in *E. coli* lacks the secretion signal sequence.

Example 6

Xyl-1 Amino Acid Sequence Analysis

A BLAST search was performed with the *A. cellulolyticus* GH10 family xylanase Xyl-1 amino acid sequence. The top hit was from a xylanase of another actinomycete, *Catenulispora acidiphila* DSM 44928, which has 75% sequence identity with Xyl-1. A recent biochemically-characterized xylanase from the actinomycete *Cellulosimicrobium* sp. HY-12 was the second best hit with 55% sequence identity to Xyl-1 (13). Multiple sequence analyses of the Xyl-1 with the above two homologs as well as other functionally characterized GH10 family xylanases showed the presence of conserved active site glutamates at positions 167 and 284 in Xyl-1 (FIG. 12). The region around the predicted active site glutamates is well-conserved in the GH10 sequences; the conserved motif around the first glutamate is DVVNE (SEQ ID NO: 23) and at the second glutamate is TELD (SEQ ID NO: 24). Xyl-1 has valine-to-alanine and leucine-to-alanine substitutions in the two regions, resulting in DVANE (SEQ ID NO: 25) and TEAD (SEQ ID NO: 26) sequences, respectively (FIG. 12). The uncharacterized *C. acidiphila* homolog also bears these substitutions.

It should be appreciated that homologous endo-beta-1,4-xylanases of the present disclosure may have a first glutamate at a position corresponding to Glu-142 of SEQ ID NO: 1. Preferably, the first glutamate is located within an amino acid region having the sequence of Asp-Val-Ala-Asn-Glu (SEQ ID NO: 25). Homologous endo-beta-1,4-xylanases of the present disclosure may have a second glutamate at a position corresponding to Glu-259 of SEQ ID NO: 1. Preferably, the second glutamate is located within an amino acid region having the sequence of Thr-Glu-Ala-Asp (SEQ ID NO: 26).

Multiple amino acid sequence alignments were performed comparing Xyl-1 with uncharacterized (C_ac, S_av), pyschrophilic (C_ad), mesophilic (C_fi), moderately thermophilic (C_sp, P_ch, S_th, T_al, T_au), and thermostable (A_ce, T_ma, U_ba) xylanases. Analysis of the amino acid composition of the different xylanases revealed that the proportions of thermolabile residues serine and threonine are markedly reduced in Xyl-1 (A_ce) compared to its closest sequence homolog C_ac (FIG. 12). A similar under-representation of these two amino acids was previously noted in the T_ma (7) protein and is thought to contribute to its high thermostability. However, most other features noted to provide thermostability to T_ma could not be identified in Xyl-1.

It was also determined that Xyl-1 contains a region of 5 amino acids, PHPLP (SEQ ID NO: 27), immediately downstream of the first active site glutamate that is different from its two closest homologs (C_ac and C_sp), as well as from other GH10 family xylanases (FIG. 12). The amino acid region includes three prolines in alternating positions. A closer look at the other xylanase sequences showed that, except for xylanases from fungi *Catenulispora acidiphila*, *Cryptococcus adeliensis*, *Phanerochaete chrysosporium*, and an uncultured bacterium (U_ba) that have a single proline close to the first active site glutamate, none of the other organisms compared have prolines within fifteen residues of the active site (FIG. 12). The unique region containing the three prolines close to the first active site glutamate may play an important role in the thermostability of Xyl-1. Proline residues influence protein folding due to their rigid conformation and have been shown to enhance protein thermostability (22). It may be that the multiple prolines around the active site of Xyl-1 may restrict main chain flexibility of the protein structure and thus increase its thermal stability.

Homologous endo-beta-1,4-xylanases of the present disclosure may have an amino acid region that includes three prolines that has an amino acid sequence that has at least 80% sequence identity with SEQ ID NO: 27. Preferably, the amino acid region has amino acid sequence SEQ ID NO: 27. Furthermore, homologous endo-beta-1,4-xylanases may have an amino acid region that includes three prolines that has an amino acid sequence homologous to SEQ ID NO: 27, where the amino acid sequence has a conservative amino acid substitution in place of any one of the three prolines. Homologous endo-beta-1,4-xylanases may also have an amino acid region that includes three prolines that has an amino acid sequence homologous to SEQ ID NO: 27, where the two non-proline amino acids of the region may be any amino acids.

Example 7

Xyl-1 Activity Assays

Materials and Methods

Xyl-1 activity was monitored using a modified version of the previously described zymogram assay (8). Briefly, proteins were separated using SDS polyacrylamide gel electrophoresis (10%). After the gel was run, it was placed in 10 mM phosphate buffer (pH 5.2) and incubated with gentle shaking at 52° C. for 15 min. The buffer was removed and replaced with 1% xylan (1% xylan from oat spelts (Sigma) in 10 mM phosphate buffer [pH 5.2]) and incubated with gentle shaking at 52° C. for 15 min. The xylan solution was removed and the gel briefly rinsed with distilled water. The gel was then placed in a solution of Congo red (0.2% in water) and incubated at room temp with gentle shaking for 20 min. The gel was destained with 1 M NaCl until the "cleared" band(s) could be visualized. To test the range of temperatures at which the enzyme was active, the in-gel assays were carried out from 4° C.-100° C. in heated or cooled water baths at pH 5.2. Activity at 0° C. was monitored in an ice bath. All solutions were preincubated to the assay temperature. The assay was also modified to test the pH range of the enzyme by using phosphate buffer from pH 2.0 to pH 10.

Results

Transformed *E. coli* cells expressing the recombinant Xyl-1 (see Example 1) were tested for xylanase activity, using oat spelt xylan as the substrate. Extracts of *E. coli* carrying the cloned gene had xylanase activity (tested at 52° C., pH 5.2), and activity was retained after a heat treatment of 65° C. for 15 min (FIG. 13). No activity was present in extracts of the strain carrying pK19 only (vector control). Activity was also observed with birchwood xylan (data not shown). Some of the protein was present in the *E. coli* culture supernatant and it exhibited electrophoretic mobility identical to that of the exported xylanase present in concentrated *A. cellulolyticus* culture supernatants from cells grown with cellobiose as the carbon source (FIG. 14).

Example 8

Optimal Activity of Xyl-1

Materials and Methods

In-gel xylanase activity was measured using the zymogram assay described in Example 7.

Activity was quantified using a modified version of the reducing sugars assay (11). Xylan substrates (oat spelt xylan or birchwood xylan, Sigma) were made by adding 1% xylan to unbuffered 10 mM phosphate solution. The slurry was incubated at 55° C. for 20 min with gentle shaking. Insoluble material was allowed to settle at room temperature. The supernatant was removed and the pH was adjusted with HCl or NaOH. Two ml of xylan suspension was added to a screw cap tube and incubated in a water bath at the desired temperature for 10 min. Xylanase was added and 200 μl samples were taken at various time points and added to 800 μl PABAH (0.5% p-hydroxybenzoic acid hydrazide in 0.5 M NaOH). Samples were boiled for exactly 5 min, allowed to cool at room temp for 10 min and the absorbance at 410 nm was determined. Results were compared to a standard curve for xylose. This assay was carried out at various temperatures and pH values to determine the temperatures and pH values at which the xylanase is active. Activity was also tested in an autoclave at 121° C. To carry out this assay, the components were mixed on ice and placed in the autoclave set to 121° C. for 10 min. The amount of reducing sugars released was determined in the presence of PABAH as described above. Protein concentrations were determined by the Bradford method (3) using bovine serum albumin as the standard.

Results

Crude cell extracts of transformed *E. coli* cells expressing the recombinant Xyl-1 had xylanase activity at temperatures from 0-100° C., as measured by zymogram assays (FIG. 15). Utilizing zymogram assays, the optimal activity of Xyl-1 was observed to be between pH 4.5-6.0, however significant activity was present at pH values from 3-9 (FIG. 16). When heated at 80° C. for 20 min in the absence of substrate, Xyl-1 retained activity (FIG. 17). Under these conditions, approximately 59% of the full activity remained (FIG. 18). However, when heated at 100° C. for 20 min in the absence of xylan, no activity remained (FIG. 18). Further investigation suggested that the presence of xylan stabilized Xyl-1 at high temperatures. Specifically, the reducing sugars assay showed that Xyl-1 has an optimal activity at approximately 90° C., which is approximately 225% higher relative to the activity determined at 55° C., when stabilized in the presence of xylan (FIG. 19).

As determined by the reducing sugars assay, the specific activity of Xyl-1 from crude cell extracts was high, at temperatures between 55 and 100° C., with incubation with substrate, and the optimal activity was at approximately 90° C. (FIG. 19). Specific activity of Xyl-1 in crude cell extracts was measured as mg of xylose per min per mg of unpurified protein. Activity was tested in an autoclave in order to test activity at a temperature higher than 100° C. (the autoclave was set at 121° C.), and some activity was retained even in the autoclave (900 μg xylose/min/mg protein).

The activity of purified Xyl-1 was also characterized over a range of temperatures and pH values using the reducing sugars assay. Purified Xyl-1 was active from 30 to 100° C., with an optimum temperature for activity of approximately 90° C. (FIG. 20). Specific activity of purified Xyl-1 was measured as mg of xylose per min per mg of purified Xyl-1. Optimal activity was observed between pH 4.5 and pH 6.0 (FIG. 20A), but significant activity was present at pH values between pH 3 and pH 9 (FIG. 20B). The optimum pH for the enzyme varied depending on the assay temperature. At 100° C., Xyl-1 was active between pH 4 to pH 6 with an optimum pH of 5.0. However, when assays were carried out from 70-90° C., the optimum pH was 6.0. It was also noted that Xyl-1 was active at higher pH values (pH 7-10) as the assay temperature decreased (FIG. 20B). The pH of the assay mix was measured at the end of each assay and no significant change in pH was found in assays over the pH 3-8 range. The pH at the end of the pH 9 assays was consistently 8.6.

Example 9

Xyl-1 Thermostability Studies

Materials and Methods

Purified Xyl-1 (1 mg/ml) was diluted 1:20 with 10 mM phosphate buffer (pH 6), or 4% oat spelt or birchwood xylan in 10 mM phosphate buffer (pH 6), mixed, and incubated on ice for a minimum of 15 min to ensure sufficient time for Xyl-1 to interact with the xylan before heat treatment. Aliquots of the control and xylan-pretreated Xyl-1 were then incubated at 90° C. for 10, 20, 40 or 60 min and immediately returned to ice. Activity was then determined using the reducing sugars assay (described in Example 5 above) at 90° C. and pH 6.

Results

The contribution of xylan substrates to the thermal stability of Xyl-1 was investigated (FIG. 21A). In the absence of xylan, Xyl-1 retained approximately 74±18%, 63±12%, 24±3%, and 5±1% of its activity after 10, 20, 40 and 60 min, respectively, at 90° C. (FIG. 21A). In contrast, no significant loss of activity was detected even after 1 hr at 90° C. in the presence of either oat spelt or birchwood xylan. Other polysaccharides that did not serve as substrates for Xyl-1 (Sigmacell cellulose, xantham gum [KELCO ZN 85192 A], and carboxymethylcellulose [Fluka]) did not stabilize Xyl-1 (data not shown). These results indicate that xylan substrates significantly stabilize purified Xyl-1 at high temperature.

Analysis of the activity of Xyl-1 after extended periods of incubation at 90° C. in the presence of oat spelt xylan indicated that the half-life of Xyl-1 is approximately 1.5 hr in the presence of the oat spelt xylan (FIG. 21B).

Example 10

Analysis of the Xylan Cleavage Pattern by Xyl-1

Materials and Methods

Products of the hydrolysis of xylans were analyzed using thin layer chromatography (TLC) as described previously (10). Oat spelt and birchwood xylans (2% in 10 mM phosphate buffer, pH 6) were each used as substrates. Purified Xyl-1 was added to the xylan substrates and incubated at 90° C. Samples were taken at various time points and quickly frozen in a dry ice-isopropanol bath and stored at −20° C. Samples were allowed to thaw on ice and were then spotted onto silica gel plates. The developing solvent was a mixture of chloroform, acetic acid, and water in a 6:7:1 ratio, respectively. The solvent front was allowed to migrate to the top of the TLC plate and then the TLC plate was allowed to air dry. To improve resolution, each chromatogram was developed this way for a total of three times. Hydrolysis products were detected by dipping the chromatogram into a solution of ethanol and sulfuric acid in a 95:5 ratio, respectively, and incubating at 105° C. for 5 min. Xylose oligomer standards (xylotriose, and xylotetraose) were obtained from Megazyme International Ireland, Ltd. (Wicklow, Ireland).

Results

Based on comparisons to the TLC mobilities of xylose, xylotriose, and xylotetraose standards (FIG. 22), the major products from the hydrolysis of birchwood xylan were identified as xylobiose and xylotetraose. Small amounts of xylose, xylotriose, and what is likely to be xylopentaose were also formed from birchwood xylan. Additional spots may represent xylan backbone xylosyl residues that are acylated or which bear sugar side groups (e.g. glucuronic acid) in the intact polysaccharide. The major products from oat spelt xylan had $R_f$ values between those of xylose and xylotriose. These may also represent acylated oligosaccharide products of Xyl-1 action or backbone xylosyl residues that carried sugar side groups (e.g., arabinosyl residues) in the intact polysaccharide.

The results confirm that Xyl-1 is an endo-acting xylanase.

Example 11

Hydrolysis of Lignocellulosic Material by Xylanase Coupled to Fermentation

Lignocellulosic material, such as switchgrass and corn stover, may be treated with a fermentation organism engineered to express the recombinant Xyl-1, extracts containing the enzyme, or purified enzyme. Treatment may be performed by combining the switchgrass or corn stover with organisms engineered to express the enzyme. Alternatively, the recombinant Xyl-1 may be added during the lignocellulose fermentation process.

REFERENCES

1. Beg, Q. K., M. Kapoor, L. Mahajan, and G. S. Hoondal. 2001. Microbial xylanases and their industrial applications: a review. Appl. Microbiol. Biotechnol. 56:326-338.
2. Butt, M. S., M. Tahir-Nadeem, Z. Ahmad, and M. T. Sultan. 2008. Xylanases and their applications in baking industry. Food Technol. Biotechnol. 46:22-31.
3. Bradford, M. M. 1976. A rapid and sensitive method for the quantitation of microgram quantities of protein utilizing the principle of protein-dye binding. Anal. Biochem. 72:248-254.
4. Collins, T., C. Gerday, and G. Fellar. 2005. Xylanases, xylanase families and extremophilic xylanases. FEMS Microbiol. Rev. 29:3-23.
5. Dodd, D., and I. O. Cann. 2009. Enzymatic deconstruction of xylan for biofuel production. GCB Bioenergy 1:2-17.
6. Giannotta, F., J. Georis, S. Rigali, M. J. Virolle, and J. Dusart. 2003. Site-directed mutagenesis of conserved inverted repeat sequences in the xylanase C promoter region from *Streptomyces* sp. ECJ. Mol. Genet. Genomics 270:337-346.
7. Ihsanawati, T. Kumasaka, T. Kaneko, C. Morokuma, R. Yatsunami, T. Sato, S, Nakamura, and N. Tanaka. 2005. Structural basis of the substrate subsite and the highly thermal stability of xylanase 10B from *Thermotoga maritima* MSB8. Proteins 61:999-1009.
8. Jung, K. H., and M. Y. Pack. 1993. Expression of a *Clostridium thermocellum* xylanase gene in *Bacillus subtilis*. Biotechnol. Lett. 15:115-120.
9. Kulkarni, N., A. Shendye, and M. Rao. 1999. Molecular and biotechnological aspects of xylanases. FEMS Microbiol. Rev. 23:411-456.
10. Lee, J.-W., J.-Y. Park, M. Kwon, and I.-G. Choi. 2009. Purification and characterization of thermostable xylanase from the brown-rot fungus *Laetiporus sulphureus*. J. Biosci. Bioeng. 107:33-37.
11. Lever, M. 1973. Colorimetric and fluorometric carbohydrate determination with p-hydroxybenzoic acid hydrazide. Biochemical Medicine 7:274-281.
12. Mohagheghi, A., K. Grohmann, M. Himmel, L. Leighton, and D. M. Updegraff. 1986. Isolation and characterization of *Acidothermus cellulolyticus* gen. nov., sp. nov., a new genus of thermophilic, acidophilic, cellulolytic bacteria. Int. J. Systematic Bact., vol. 36, no. 3, pp. 435-443.
13. Oh, H.-W., S.-Y. Heo, D. Y. Kim, D.-S. Park, K. S. Bae, and H.-Y. Park. 2008. Biochemical characterization and sequence analysis of a xylanase produced by an exo-symbiotic bacterium of *Gryllotalpa orientalis*, *Cellulosimicrobium* sp. HY-12. Antonie van Leeuwenhoek 93:437-442.
14. Polizeli, M. L. T. M., A. C. S. Rizzatti, R. Monti, H. F. Terenzi, J. A. Jorge, and D. S. Amorim. 2005. Xylanases from fungi: properties and industrial applications. Appl. Microbiol. Biotechnol. 67:577-591.
15. Pospiech, A., and B. Neumann. 1995. A versatile quick-prep of genomic DNA from gram-positive bacteria. Trends Genet. 11:217-218.
16. Pridmore, R. D. 1987. New and versatile cloning vectors with kanamycin-resistance marker. Gene 56:309-312.

17. Rice, P., I. Longden, and A. Bleasby. 2000. EMBOSS: The European Molecular Biology Open Software Suite. Trends Genet. 16:276-277.
18. Sambrook, J., E. F. Fritch, and T. Maniatis. 1989. Molecular Cloning: a laboratory manual, 2nd ed. Cold Spring Harbor Laboratory, Cold Spring Harbor, N.Y.
19. Shiang, M., J. C. Linden, A. Mohagheghi, K. Grohmann, and M. E. Himmel. 1991. Enhanced production of cellulase using *Acidothermus cellulyticus* in fed-batch culture. Appl. Microb. Biotech. 34:591-597.
20. Strohl, W. R. 1992. Compilation and analysis of DNA sequences associated with apparent *Streptomyces* promoters. Nucleic Acids Res. 20:961-974.
21. Subramaniyan, S., and P. Prema. 2002. Biotechnology of microbial xylanases: enzymology, molecular biology, and application. Crit. Rev. Biotechnol. 22:33-64.
22. Watanabe, K., Y. Hata, H. Kizaki, Y. Katsube, and Y. Suzuki. 1997. The refined crystal structure of *Bacillus cereus* oligo-1,6-glucosidase at 2.0 Å resolution: structural characterization of proline-substitution sites for protein thermostabilization. J. Mol. Biol. 269:42-53.

We claim:

1. A method for hydrolyzing lignocellulose, the method comprising contacting lignocellulose with a recombinant endo-beta-1,4-xylanase comprising an amino acid sequence with at least 90% sequence identity to SEQ ID NO: 1, wherein the lignocellulose is contacted with the recombinant xylanase at a temperature of at least 80° C. and a pH range from 3.0 to 9.0, wherein said xylanase comprises a Glu at a position corresponding to position 142 of SEQ ID NO: 1 and a Glu at a position corresponding to position 259 of SEQ ID NO: 1, wherein said xylanase comprises at least one peptide having the sequence Pro-Xaa$_1$-Pro-Xaa$_2$-Pro (SEQ ID NO: 40), wherein Xaa$_1$ and Xaa$_2$ are each independently selected from the group consisting of no amino acid, any one amino acid, any two amino acids, and any three amino acids, wherein said at least one peptide is at least 80% sequence identical to the peptide of SEQ ID NO: 27, and wherein said at least one peptide is located between the Glu at the position corresponding to position 142 of SEQ ID NO: 1 and the Glu at the position corresponding to position 259 of SEQ ID NO: 1.

2. The method of claim 1, wherein the pH range is from 4.5 to 6.0.

3. The method of claim 1, wherein the lignocellulose is contacted with the protein at a temperature of at least 90° C.

4. The method of claim 1, wherein the amino acid sequence of the recombinant xylanase is at least 93% identical to SEQ ID NO: 1.

5. The method of claim 1, wherein the amino acid sequence of the recombinant xylanase is at least 95% identical to SEQ ID NO: 1.

6. The method of claim 1, wherein the amino acid sequence of the recombinant xylanase is at least 97% identical to SEQ ID NO: 1.

7. The method of claim 1, wherein the amino acid sequence of the recombinant xylanase is SEQ ID NO: 1.

8. The method of claim 1, wherein the amino acid sequence comprises one or more of SEQ ID NO: 23, SEQ ID NO: 24, SEQ ID NO: 25, SEQ ID NO: 26, or SEQ ID NO: 27.

9. The method of claim 1, wherein the recombinant xylanase has a molecular weight of between 40 and 48 kD.

10. The method of claim 1, wherein a source of the lignocellulose is selected from the group consisting of: birchwood, oat spelt, switchgrass, corn stover, miscanthus, energy cane, sorghum, eucalyptus, willow, bagasse, hybrid poplar, short-rotation woody crop, conifer softwood, crop residue, yard waste, and a combination thereof.

11. The method of claim 1, wherein the recombinant xylanase further comprises a signal peptide having the amino acid sequence of SEQ ID NO: 2.

* * * * *